United States Patent
Strobel et al.

(10) Patent No.: US 10,869,482 B2
(45) Date of Patent: Dec. 22, 2020

(54) MUSCODOR ALBUS STRAIN PRODUCING VOLATILE ORGANIC COMPOUNDS AND METHODS OF USE

(71) Applicant: Marrone Bio Innovations, Inc, Davis, CA (US)

(72) Inventors: Gary Strobel, Bozeman, MT (US); Vu Phong Bui, Sacramento, CA (US); Hai Su, Woodland, CA (US); Phyllis Himmel, Davis, CA (US); Pamela Marrone, Davis, CA (US); Lijuan Xing, Newark, DE (US)

(73) Assignee: Marrone Bio Innovations, Inc., Davis, CA (US)

( * ) Notice: Subject to any disclaimer, the term of this patent is extended or adjusted under 35 U.S.C. 154(b) by 327 days.

(21) Appl. No.: 14/789,742

(22) Filed: Jul. 1, 2015

(65) Prior Publication Data
US 2015/0313242 A1 Nov. 5, 2015

Related U.S. Application Data

(63) Continuation of application No. 13/843,755, filed on Mar. 15, 2013, now abandoned.

(60) Provisional application No. 61/705,312, filed on Sep. 25, 2012.

(51) Int. Cl.
| | | |
|---|---|---|
| A01N 63/30 | (2020.01) | |
| C12R 1/645 | (2006.01) | |
| C12P 1/02 | (2006.01) | |
| A01N 27/00 | (2006.01) | |
| A01N 35/02 | (2006.01) | |
| A01N 37/02 | (2006.01) | |
| A01N 37/06 | (2006.01) | |
| A01N 31/02 | (2006.01) | |
| A01N 31/04 | (2006.01) | |
| A01N 31/14 | (2006.01) | |
| C12N 1/14 | (2006.01) | |
| A01N 25/00 | (2006.01) | |

(52) U.S. Cl.
CPC ............ *A01N 63/30* (2020.01); *A01N 25/00* (2013.01); *A01N 27/00* (2013.01); *A01N 31/02* (2013.01); *A01N 31/04* (2013.01); *A01N 31/14* (2013.01); *A01N 35/02* (2013.01); *A01N 37/02* (2013.01); *A01N 37/06* (2013.01); *C12N 1/14* (2013.01); *C12P 1/02* (2013.01); *C12R 1/645* (2013.01)

(58) Field of Classification Search
CPC ........ A01N 63/04; A01N 65/00; A01N 37/06; A01N 31/04; A01N 27/00; A01N 31/02; A01N 31/14; A01N 35/02; A01N 37/02; A01N 63/30; A01N 25/00; A01N 63/32; A01N 63/34; A01N 63/36; A01N 63/38; A01N 63/40; A01N 63/50; A01N 63/60; A01N 45/02; A01N 2300/00; C12N 1/14; C12P 1/02; C12R 1/645
See application file for complete search history.

(56) References Cited

U.S. PATENT DOCUMENTS

| | | | | |
|---|---|---|---|---|
| 5,989,543 | A | * | 11/1999 | Davide .................... C12R 1/79 424/93.5 |
| 6,911,338 | B2 | | 6/2005 | Strobel et al. |
| 7,070,985 | B2 | | 7/2006 | Strobel et al. |
| 7,267,975 | B2 | | 9/2007 | Strobel et al. |
| 7,341,862 | B2 | | 3/2008 | Strobel et al. |
| 7,754,203 | B2 | | 7/2010 | Strobel et al. |
| 7,858,362 | B2 | | 12/2010 | Phillips et al. |
| 8,093,024 | B2 | | 1/2012 | Strobel et al. |
| 2004/0141955 | A1 | | 7/2004 | Strobel et al. |
| 2010/0255124 | A1 | | 10/2010 | Green et al. |
| 2010/0272690 | A1 | | 10/2010 | Gandhi et al. |
| 2011/0182862 | A1 | | 7/2011 | Green et al. |
| 2011/0257009 | A1 | | 10/2011 | Seitz et al. |
| 2011/0287471 | A1 | | 11/2011 | Strobel et al. |
| 2012/0058058 | A1 | * | 3/2012 | Jimenez ................. A01N 51/00 424/45 |

FOREIGN PATENT DOCUMENTS

WO WO 2010/132509 A2 11/2010

OTHER PUBLICATIONS

David Ezra et al.; "New endophytic isolates of Muscodor albus, a volatile-antibiotic-producing fungus"; DOI 10.1099/mic.0.27334-0; Microbiology (2004) SGM, 150, pp. 4023-4031.
Agraquest, Inc., *Muscodor™ a new biofumigant as an alternative to methyl bromide*. 2005 Annual International Research Conference on Methyl Bromide Alternatives and Emission Reductions, San Diego, CA.
Atmosukarto, I., et al., *Isolation and characterization of Muscodor albus I-41.3s, a volatile antibiotic producing fungus*. Plant Science, 2005. 169(5): p. 854-861.
Banerjee, D., et al., *Muscodor albus strain GBA, an endophytic fungus of Ginkgo biloba from United States of America, produces volatile antimicrobials*. Mycology, 2010. 1(3): p. 179-186.
Baysal, F., et al., *Effects of Muscodor, Serenade and conventional fungicides on Rhizoctonia root and hypocotyl rot and clubroot of radish*. Phytopathology, 2007. 97(7)(Supplement): S9.

(Continued)

*Primary Examiner* — John Pak
*Assistant Examiner* — Andriae M Holt
(74) *Attorney, Agent, or Firm* — Chainey P. Singleton; Ying-Horng Liu; Singleton Law, PLLC

(57) ABSTRACT

Disclosed herein is an isolated *Muscodor albus* strain producing volatile organic compounds such as aristolene, 3-octanone and/or acetic acid ester, as well as cultures of said strain and compositions, metabolites and volatiles derived from said strain or culture as well as methods of obtaining said compositions, metabolites and volatiles and their methods of use for controlling pests. Also disclosed are artificial compositions having the same components and uses as the volatiles derived from the strain. A method for capturing and sampling the volatiles is also disclosed.

6 Claims, 7 Drawing Sheets

(56) References Cited

OTHER PUBLICATIONS

Benson, D.M., and K.C. Parker, *Efficacy of fungicides and biopesticides for management of phytophthora crown and root rot of gerber daisy.* Plant Health Progress, 2011. DOI:10.1094/PHP-2011-0512-)1-RS.

Braun, P.G., et al., *Muscodor albus volatiles control toxigenic fungi on media under controlled atmosphere in storage conditions.* Can. J. Plant Pathol., 2007. 29:89.

Camp, A.R., et al., *Efficacy of Muscodor albus for the Control of Phytophthora Blight of Sweet Pepper and Butternut Squash.* Plant Disease, 2008. 92(11): p. 1488-1492.

Campos, V.P., et al., *Volatiles produced by interacting microorganisms potentially useful for the control of plat pathogens.* Cienc. Agrotec., Lvras, 2010. 34(3): p. 525-535.

Corcuff, R., et al. *Biofumigation potential of Muscodor albus volatiles in the storage of potato tubers. in 2006 APS Annual Meeting.* 2006. Quebec City, Canada: Phytopathology. 96(6)(Supplement): S26.

Corcuff, R., et al., *Effect of water activity on the production of volatile organic compounds by Muscodor albus and their effect on three pathogens in stored potato.* Fungal Biology, 2011. 115(3): p. 220-227.

Daisy, B., et al., *Muscodor vitigenus anam. nov., an endophyte from Paullinia paullinioides.* Mycotaxon, 2002. 84: p. 39-50.

Daisy, B.H., et al., *Naphthalene, an insect repellent, is produced by Muscodor vitigenus, a novel endophytic fungus.* Microbiology (SGM), 2002. 148: p. 3737-3741.

Ezra, D. and G.A. Strobel, *Effect of substrate on the bioactivity of volatile antimicrobials produced by Muscodor albus.* Plant Science, 2003. 165(6): p. 1229-1238.

Ezra, D., et al., *Proton transfer reaction-mass spectrometry as a technique to measure volatile emissions of Muscodor albus.* Plant Science, 2004. 166(6): p. 1471-1477.

Ezra, D., et al., *New endophytic isolates of Muscodor albus, a volatile-antibiotic-producing fungus.* Microbiology (SGM), 2004. 150: p. 4023-4031.

Ezra, D., et al., *Development of methods for detection and Agrobacterium-mediated transformation of the sterile, endophytic fungus Muscodor albus.* Biocontrol Science and Technology, 2010. 20(1): p. 83-97.

Freitas, P., *Biofumigation with Muscodor albus for postharvest control of gray mold rot and Salmonella contaminiation of tomatoes.* Phytopathology, 2005. 95(6)(Supplement): S31.

Gabler, F.M., et al., *Influence of packaging, termperature, and incoulation timing on the effectiveness of biofirmitation with Muscodor albus to control postharvest gray mold on table grapes.* Phytopathology, 2005. 95(6)(Supplement): S123 (In Errata).

Gabler, F.M., et al., *Influence of temperature, inoculation interval, and dosage on biofumigation with Muscodor albus to control postharvest gray mold on grapes.* Plant Disease, 2006. 90(8): p. 1019-1025.

Gabler, F.M., et al., *Integrated control of table grape postharvest gray mold by ozone and Muscodor albus fumigation.* Phytopathology, 2007. 97(7)(Supplement): S78.

Gabler, F.M., et al., *Integration of continuous biofumigation with Muscodor albus with pre-cooling fumigation with ozone or sulfur dioxide to control postharvest gray mold of table grapes.* Postharvest Biology and Technology, 2010. 55(2): p. 78-84.

Gao, F., et al., *Mechanisms of fungal endophytes in plant protection against pathogens.* African J. Microbiology Res., 2010. 4(13): p. 1346-1351.

Goates, B.J. and J. Mercier, *Mortality of Tilletia spp. teliospores caused by volatiles from the biofumigant fungus Muscodor albus.* Phytopathology, 2007. 97(7)(Supplement): S41.

Goates, B.J. and J. Mercier, *Effect of biofumigation with volatiles from Muscodor albus on the viability of Tilletia spp. teliospores.* Canadian Journal of Microbiology, 2009. 55(2): p. 203-206.

Goates, B.J. and J. Mercier, *Control of common bunt of wheat under field conditions with furrow treatments with the biofumigant fungus Muscodor albus.* Phytopathology, 2009. 99(6)(Supplement): S43.

Goates, B.J. and J. Mercier, *Control of common bunt of wheat under field conditions with the biofumigant fungus Muscodor albus.* European Journal of Plant Pathology, 2011. 131(3): p. 403-407.

Gonzalez, M.C., et al., *Muscodor yucatanensis, a new endophytic ascomycete from Mexican chakah, Bursera simaruba.* Mycotaxon, 2009. 110: p. 363-372.

Grimme, E., *Effects of mycofumigation using Muscodor albus and Muscodor roseus on diseases of sugar beet and chrysanthemum.* Montana State University Master of Science Thesis in Plant Pathology, Bozeman, Montana, 2004.

Grimme, E., et al., *Comparison of Muscodor albus volatiles with a biorational mixture for control of seedling diseases of sugar beet and root-knot nematode on tomato.* Plant Disease, 2007. 91(2): p. 220-225.

Grimme, E., et al., *Effects of volatile organic compounds of Muscodor albus on Verticillium dahliae and Colletotrichum coccodes of potato.* Phytopathology, 2007. 97(7)(Supplement): S43.

Gunatilaka, A.A.L., *Natural products from plant-associated microorganisms; distribution, structural diversity, bioactivity, and implications of their occurrence.* J. Nat. Prod., 2006. 69: p. 509-526.

Gurel, F.B., and S.A. Miller, *Efficacy of biopesticides and fungicides against pre- and post-emergence damping-off of vegetable seedlings by Pythium aphanidernatum.* Phytopathology, 2008. 98(6)(Supplement):S19.

Highland, H. and C. Yuan, *The use of the biofumigant Muscodor albus to reduce root disease and improve growth in transplant vegetable production.* Phytopathology, 2005. 95(6)(Supplement): S42.

Highland, H.B., *QRD 300: Muscodor albus a new biofumigant for use as an alternative to methyl bromide.* 2006 Annual International Research Conference on Methyl Bromide Alternatives and Emission Reductions, Orlando FL.

Insam, H. and M.S.A. Seewald, *Volatile organic compounds (VOCs) in soils.* Biol. Fertil. Soils, 2010. 46: p. 199-213.

Ji, P., et al., *Efficacy of several biorational compounds for control of bacterial wilt of tomato under greenhouse conditions.* Phytopathology, 2006. 96(6)(Supplement): S54.

Jimenez, J. and J. Mercier, *Optimization of volatile compound production from rye grain culture of Muscodor albus for postharvest fumigation.* Phytopathology, 2005. 95(6)(Supplement): S48.

Jimenez, J. and D.C. Manker, *Nematicidal activity of Muscodor albus.* J. Nematology, 2007. 39(1): 101.

Kirk, P. Index Fungorum—Names Record. 2008; Available from: http://www.indexfungorum.org/Names/NamesRecord.asp?RecordID-28513.

Kudalkar, P., et al., *Muscodor sutura, a novel endophytic fungus with volatile antibiotic activities.* Mycoscience, 2012. 53(4): p. 319-325.

Lacey, L.A., and L.G. Neven, *The potential of the fungus, Muscodor albus, as a microbial control agent of potato tuber moth (Lepidoptera : Gelechiidae) in stored potatoes.* Journal of Invertebrate Pathology, 2006. 91(3): p. 195-198.

Lacey, L.A., et al., *The effect of temperature and duration of exposure of potato tuber moth (Lepidoptera : Gelechiidae) in infested tubers to the biofumigant fungus Muscodor albus.* Journal of Invertebrate Pathology, 2008. 97(2): p. 159-164.

Lacey, L.A., et al., *Efficacy of the Biofumigant Fungus Muscodor albus (Ascomycota: Xylariales) for Control of Codling Moth (Lepidoptera: Tortricidae) in Simulated Storage Conditions.* Journal of Economic Entomology, 2009. 102(1): p. 43-49.

Macias-Rubalcava, M.L., et al., *Allelochemical Effects of Volatile Compounds and Organic Extracts from Muscodor yucatanensis, a Tropical Endophytic Fungus from Bursera simaruba.* Journal of Chemical Ecology, 2010. 36(10): p. 1122-1131.

Mends, M.T., et al., *An endophytic Nodulisporiujm sp. producing volatile organic compounds having bioactivity and fuel potential.* J. Pet. Environ. Biotechnol., 2012. 3: p. 1-7.

Mercier, J. and J.I. Jimenez, *Control of fungal decay of apples and peaches by the biofumigant fungus Muscodor albus.* Postharvest Biology and Technology, 2004. 31(1): p. 1-8.

(56) References Cited

OTHER PUBLICATIONS

Mercier, J. and D.C. Manker, *Biocontrol of soil-borne diseases and plant growth enhancement in greenhouse soilless mix by the volatile-producing fungus Muscodor albus*. Crop Protection, 2005. 24(4): p. 355-362.
Mercier, J., et al., *Biofumitation with Muscodor albus pads for controlling decay in commercial table grape cartons*. HortScience, 2005. 40: p. 1144.
Mercier, J. and J.L. Smilanick, *Control of green mold and sour rot of stored lemon by biofumigation with Muscodor albus*. Biological Control, 2005. 32(3): p. 401-407.
Mercier, J., *Biofumigation with Muscodor albus, a new tool for postharvest disease control*. Phytopathology, 2005. 95(6)(Supplement): S141.
Mercier, J. and J.I. Jimenez, *Control of building mold colonization of drywall with volatiles from Muscodor albus*. Phytopathology, 2006. 96(6)(Supplement): S78.
Mercier, J. and J.I. Jimenez, *Demonstration of biofumigation activity of Muscodor albus in soil substrates*. Phytopathology, 2006. 96(6)(Supplement): S78.
Mercier, J., et al., *Soil fumigation with perlite colonized by the volatile-producing fungus Muscodor albus*. Phytopathology, 2007. 97(7)(Supplement): S75.
Mercier, J. and J.I. Jimenez, *Potential of the volatile-producing fungus Muscodor albus for control of building molds*. Canadian Journal of Microbiology, 2007. 53(3): p. 404-410.
Mercier, J., et al., *Development of the volatile-producing fungus Muscodor albus Worapong, Strobel, and Hess as a novel antimicrobial biofumigant*. Revista Mexicana de Fitopatologia, 2007. 25(2): p. 173-179.
Mercier, J. and J.I. Jimenez, *Demonstration of the biofumigation activity of Muscodor albus against Rhizoctonia solani in soil and potting mix*. Biocontrol, 2009. 54(6): p. 797-805.
Mercier, J., et al., *In-package use of Muscodor albus volatile-generating sachets and modified atmosphere liners for decay control in organic table grapes under commercial conditions*. Fruits, 2010. 65(1): p. 31-38.
Merteley, J.C., et al., *Effect of the biofumigant Muscador on strawberry plant growth and yield*. Phytopathology, 2006. 96(6)(Supplement): S78.
Mitchell, A.M., et al., *Muscodor crispans, a novel endophyte from Ananas ananassoides in the Bolivian Amazon*. Fungal Diversity, 2008. 31: p. 37-43.
Mitchell, A.M., et al., *Volatile antimicrobials from Muscodor crispans, a novel endophytic fungus*. Microbiology (SGM), 2010. 156: p. 270-277.
Naik, B.S. and Y.L. Krishnamurthy, *Endophytes: the real untapped high energy biofuel resource*. Current Science, 2010. 98: p. 883.
Osono, T. and H. Masuya, *Endophytic fungi associated with leaves of Betulaceae in Japan*. Canadian Journal of Microbiology, 2012. 58(4): p. 507-515.
Ownley, B.H., et al., *Endophytic fungal entomopathogens with activity against plant pathogens: ecology and eveloution*. BioControl, 2010. 55: p. 113-128.
Prange, R.K., et al., *Perspectives on postharvest biopesticides and storage technologies for organic produce*. HortScience, 2006. 41: p. 301-303.
Ramin, A.A., et al., *In vitro effects of Muscodor albus and three volatile components on growth of selected postharvest microorganisms*. HortScience, 2005. 40(7): p. 2109-2114.
Riga, E., et al., *The potential of the fungus Muscodor albus as a bio-control agent against economically important plant-parasitic nematodes of potatoes in Washington state*. J. of Nematology, 2007. 39(1): 98.
Riga, E., et al., *Muscodor albus, a potential biocontrol agent against plant-parasitic nematodes of economically important vegetable crops in Washington State, USA*. Biological Control, 2008. 45(3): p. 380-385.

Romanazzi, G., et al., *Recent advances on the use of natural and safe alternatives to conventional methods to control postharvest gray mold of table grapes*. Postharvest Biology and Technology, 2012. 63: p. 141-147.
Ruark, S.J., and B.B. Shew, *Efficacy of biological and other novel seed treatments suitable for use in organic peanut production systems*. Phytopathology, 2008. 98(6)(Supplement): S137.
Ruark, S.J. and B.B. Shew, *Evaluation of microbial, botanical, and organic treatments for control of peanut seddling diseases*. Plant Dis., 2010. 94: p. 445-454.
Samtani, J.B., et al., *Evaluation of non fumigant alternatives to methyl bromide for weed cnotrol and crop yield in California strawberries (Fragaria ananassa L.)*. Crop Protection, 2011. 30: p. 45-51.
Saunders, M. et al., *Exploring the evolutionary ecology of fungal endophytes in agricultural systems: using functional traits to reveal mechanisms in community process*. Evolutionary Applications, 2010. 3: p. 525-537.
Schnabel, G. and J. Mercier, *Use of a Muscodor albus pad delivery system for the management of brown rot ofpeach in shipping cartons*. Postharvest Biology and Technology, 2006. 42(1): p. 121-123.
Schotsmans, W.C., et al., *Temperature and controlled atmosphere effects on efficacy of Muscodor albus as a biofumigant*. Biological Control, 2008. 44(1): p. 101-110.
Sopalun, K., et al., *A record of Muscodor albus, an endophyte from Myristica fragrans in Thailand*. Mycotaxon, 2003. 88: p. 239-247.
Stinson, A.M., et al., *Mycofumigation with Muscodor albus and Muscodor roseus for control of seedling diseases of sugar beet and Verticillium wilt of eggplant*. Plant Disease, 2003. 87(11): p. 1349-1354.
Stinson, M., et al., *An endophytic Gliocladium sp. of Eucryphia cordifolia producing selective volatile antimicrobial compounds*. Plant Science, 2003. 165: p. 913-922.
Strobel, G.A., et al., *Volatile antimicrobials from Muscodor albus, a novel endophytic fungus*. Microbiology-Sgm, 2001. 147: p. 2943-2950.
Strobel, G.A., *Rainforest endophytes and bioactive products*. Critical Reviews in Biotechnology, 2002. 22: p. 315-333.
Strobel, G. and B. Daisy, *Bioprospecting for microbial endophytes and their natural products*. Microbiology and Molecular Biology Reviews, 2003. 67(4): p. 491-520.
Strobel, G.A., *Endophytes as sources of bioactive products*. Microbes and Infection, 2003. 5: p. 535-544.
Strobel, G.A., et al., *Natural products from endophytic microorganisms*. J. Nat. Prod., 2004. 67: p. 257-268.
Strobel, G., *Plant-symbiont relationships: What's up with a stinky white fungus*. Phytopatholo , 2005. 95 (6)(Supplement): S138.
Strobel, G., *Harnessing endophytes for industrial microbiology*. Current Opinion in Microbiology, 2006. 9(3): p. 240-244.
Strobel, G., *Muscodor albus and its biological promise*. Journal of Industrial Microbiology & Biotechnology, 2006. 33(7): p. 514-522.
Strobel, G.A., et al., *Muscodor albus E-6, an endophyte of Guawma ulmifolia making volatile antibiotics: isolation, characterization and experimental establishment in the host plant*. Microbiology (SGM), 2007. 153: p. 2613-2620.
Strobel, G.A., et al., *Synergism among volatile organic compounds resulting in increased antibiosis in Oidium sp*. FEMS Microbiol. Lett., 2008. 283: p. 140-145.
Strobel, G., *Muscodor species endophytes with biological promise*. Phytochem. Rev., 2011. 10: p. 165-172.
Strobel, G.A., *Muscodor albus—the anatomy of an important biological discovery*. Microbiology Today, 2012. p. 108-111.
Suslow, T., et al., *Efficacy of volatilese produced by Muscodor albus in the disinfection of edible horticultural commodities*. RTI Technical Abstracts, 2004. Abstract T07.
Suszkiw, J. and M. Wood, *Fungal fumes clear out crop pests*. Agricultural Research, Feb. 2010. p. 20-21.
Suwannarach, N., et al., *Muscodor cinnamomi, a new endophytic species from Cinnamomum bejolghota*. Mycotaxon, 2010. 114: p. 15-23.

(56) References Cited

OTHER PUBLICATIONS

Worapong, J., et al., *Muscodor albus anam. gen. et sp nov., an endophyte from Cinnamomum zeylanicum*. Mycotaxon, 2001. 79: p. 67-79.
Worapong, J., et al., *Muscodor roseus anam. sp nov., an endophyte from Grevillea pteridifolia*. Mycotaxon, 2002. 81: p. 463-475.
Worapong, J. and G.A. Strobel, *Biocontrol of a root rot of kale by Muscodor albus strain MFC2*. Biocontrol, 2009. 54(2): p. 301-306.
Yee, W.L., et al., *Pupal Mortality and Adult Emergence of Western Cherry Fruit Fly (Diptera: Tephritidae) Exposed to the Fungus Muscodor albus (Xylariales: Xylariaceae)*. Journal of Economic Entomology, 2009. 102(6): p. 2041-2047.
Yuan, Z.L., et al., *Distinctive Endophytic Fungal Assemblage in Stems of Wild Rice (Oryza granulata) in China with Special Reference to Two Species of Muscodor (Xylariaceae)*. Journal of Microbiology, 2011. 49(1): p. 15-23.
Yuan, Z.L., et al., *Current perspectives on the volatile-producing fungal endophytes*. Critical Reviews in Biotechnology, 2012. 32(4): p. 363-373.
Zhang, C.L., et al., *Muscodor fengyangensis sp. nov. from southeast China: morphology, physiology and production of volatile compounds*. Fungal Biology, 2010. 114(10): p. 797-808.
International Search Report and Written Opinion of the International Searching Authority issued in International App. No. PCT/US2013/061531 dated Dec. 26, 2013 (18 pages).

\* cited by examiner

MUSCODOR ALBUS STRAIN PRODUCING VOLATILE ORGANIC COMPOUNDS AND METHODS OF USE

CROSS REFERENCE TO RELATED APPLICATION

This application is a continuation application of U.S. application Ser. No. 13/843,755 filed Mar. 15, 2013, which claims the benefit under 35 U.S.C. § 119(e) to U.S. Provisional Application No. 61/705,312, filed Sep. 25, 2012, both of which are hereby incorporated by reference.

TECHNICAL FIELD

Disclosed herein is an isolated *Muscodor albus* strain producing volatile organic compounds (VOCs) as well as cultures of said strain and compositions, and metabolites derived from said strain or culture as well as methods of obtaining said compositions, metabolites and volatiles and their methods of use for controlling pests and phytopathogenic infection.

BACKGROUND OF THE INVENTION

Natural products are substances produced by microbes, plants, and other organisms. Microbial natural products offer an abundant source of chemical diversity, and there is a long history of utilizing natural products for pharmaceutical purposes. Despite the emphasis on natural products for human therapeutics, where more than 50% are derived from natural products, only 11% of pesticides are derived from natural sources. Nevertheless, natural product pesticides have a potential to play an important role in controlling pests in both conventional and organic farms. Secondary metabolites produced by microbes (bacteria, actinomycetes and fungi) provide novel chemical compounds which can be used either alone or in combination with known compounds to effectively control insect pests and to reduce the risk for resistance development. In particular endophytic fungi and bacteria, fungi and bacteria living with the tissues of host plants, specifically on the intracellular spaces of plant tissues and coexist with their hosts without any pathogenic symptoms have been found to be a rich source of bioactive natural products.

There are several well-known examples of microbial natural products that are successful as agricultural insecticides (Thompson et al., 2000, Pest Management Science 56: 696-702; Arena et al., 1995, Journal of Parasitology 81: 286-294; Krieg et al. 1983, Z. Angew. Entomol. 96: 500-508). A number of fungal species are known to produce concentrations of volatile antibiotics (see, for example, Strobel, 2006, J. Ind. Microbiol. Biotechnol. 33: 514-22 for review).

Species of endophytic fungi, *Muscodor* have been disclosed, particularly, *Muscodor albus* strain CZ 620, *Muscodor roseus* A3-5 and *Muscodor viigenus* 2116 (see, for example, Strobel, 2006, J. Ind. Microbiol. Biotechnol. 33: 514-22; Strobel, 2012, Microbiol. Today 39-108-109; U.S. Pat. Nos. 6,911,338, 7,267,975). Volatiles produced by these *Muscodor* strains have been found to possess nematocidal, insecticidal, acaricidal, fungicidal and bactericidal activity (see, for example, Lacey et al., 2008, J. Invertebrate Pathology 97:159-164; Strobel, 2006, J. Ind. Microbiol. Biotechnol. 33: 514-22; Strobel, 2012, Microbiol. Today (May 2012 108-109; Riga et al., 2008, Biological Control 45:380-385; WO2010/132509; U.S. Pat. Nos. 6,911,338, 7,267,975, 7,754,203, 8,093,024).

It is an object to provide additional *Muscodor* strains that have enhanced beneficial biological activity.

SUMMARY OF THE INVENTION

Provided is an isolated *Muscodor* strain which
(a) produces a product, particularly volatile compounds including but not limited to small alcohols, esters, acids, ketones as well as hydrocarbon and particularly comprising at least one of 3-octanone, (−) aristolene, propanoic acid and/or an ester form, acetic acid ester and in particular, acetic acid, 2-methylpropyl ester and/or acetic acid, 2-phenylethyl ester;
(b) produces volatile compounds that possess fungicidal activity, wherein said culture produces a product that has at least about 1.5 fold more inhibitory effect on *Fusarium* and particularly, *Fusarium oxysporum*, growth than *Muscodor albus* strain CZ 620;
(c) produces volatile compounds which possess nematicidal activity, wherein said culture produces a product that has at least about 4 fold more of an effect on mortality on *Meloidogyne* spp. than *Muscodor albus* strain CZ 620.
(d) produces volatile compounds which exhibit insecticidal activity and in particular with respect to armyworm eggs.

In a related aspect, provided is (a) a substantially pure culture or whole cell broth comprising or (b) cell fraction, supernatant, substance, compound, metabolite or volatile derived from the *Muscodor* strain set forth above. *Muscodor* culture has at least one of the identifying characteristics of *Muscodor albus* strain SA-13 (NRRL Accession No. B-50774). In a more particular embodiment, the *Muscodor* culture or strain has all of the identifying characteristics of *Muscodor albus* strain SA-13 (NRRL Accession No. B-50774).

In a particular embodiment, provided is a composition comprising the substantially pure culture or whole cell broth comprising said strain or cell fraction, supernatant, substance, compound, metabolite or volatile derived from the said strain. In a specific embodiment the composition comprises a plurality of substances, compounds, metabolites and/or volatiles derived from the culture.

In a related aspect, a method is provided for identifying one or more volatile organic compounds produced by a *Muscodor* strain. In the method a volatile composition produced by the growing culture, such as the *Muscodor* strain set forth above, is captured by contacting a gas stream containing the volatile substance or substances with a material or phase capable of removing the volatiles from the gas stream and then recovering the volatiles for analyses. The method may further comprise capturing said volatiles on a nonionic resin that acts as a molecular weight exclusion vehicle and identifying compounds captured on said resin In another aspect of the invention, a composition comprising a mixture containing the volatile organic compounds (VOCs) produced by the culture or strain and the use of such mixtures to control plant pathogens and infestations are disclosed. The composition may be a reconstituted mixture of products produced by said strain or may be an artificial mixture of VOCs.

In one embodiment, the composition comprises:
Ethanol;
Propanol;
2-Butanone, 4-hydroxy-;
Ethyl Acetate;
Propanoic acid, ethyl ester;
1-Butanol, 3-methyl-;
1-Butanol, 2-methyl-;
Propanoic acid, 2-methyl-, ethyl ester;
Butanoic acid, 2-methyl-, methyl ester;
Butanoic acid, 2-methyl-, ethyl ester;
Propanoic acid, 2-methyl-, butyl ester;
1-Butanol, 3-methyl-, acetate;
Ethyl tiglate;
Phenylethyl Alcohol;
Azulene, 1,2,3,5,6,7,8,8a-octahydro-1,4-dimethyl-7-(1-methylethenyl)-, [1S-(1.alpha.,7.alpha.,8a.beta.)]-.
And at least one of: Propanoic acid, 2-methyl-, methyl ester; Acetic acid, 2-methylpropyl ester; 1-Butanol, 2-methyl-, acetate; Propanoic acid, 2-methyl-, butyl ester; Benzene, methoxy-; 3-Octanone; Propanoic acid, 2-methyl-, 3-methylbutyl ester; Acetic acid, 2-phenylethyl ester; (−) Aristolene; Cyclohexane, 1-ethenyl-1-methyl-2,4-bis(1-methylethenyl)-; Azulene, 1,2,3,4,5,6,7,8-octahydro-1,4-dimethyl-7-(1-methylethenyl)-, (1S-(1.alpha.,4.alpha.,7.alpha.)]-; Bicyclo[5.3.0]decane, 2-methylene-5-(1-methylvinyl)-8-methyl-;
and optionally a carrier, diluent or adjuvant.

In a specific embodiment, the composition comprises
Ethanol;
Propanol;
2-Butanone, 4-hydroxy-;
Ethyl Acetate;
Propanoic acid, 2-methyl-, methyl ester;
Propanoic acid, ethyl ester;
1-Butanol, 3-methyl-;
1-Butanol, 2-methyl-;
Propanoic acid, 2-methyl-, ethyl ester;
Acetic acid, 2-methylpropyl ester;
Butanoic acid, 2-methyl-, methyl ester;
Butanoic acid, 2-methyl-, ethyl ester;
Propanoic acid, 2-methyl-, butyl ester;
1-Butanol, 3-methyl-, acetate;
1-Butanol, 2-methyl-, acetate;
Propanoic acid, 2-methyl-, butyl ester;
Benzene, methoxy-;
Ethyl tiglate;
3-Octanone;
Propanoic acid, 2-methyl-, 3-methylbutyl ester;
Phenylethyl Alcohol;
Acetic acid, 2-phenylethyl ester;
(−)Aristolene;
Cyclohexane, 1-ethenyl-1-methyl-2,4-bis(1-methylethenyl)-;
Azulene, 1,2,3,4,5,6,7,8-octahydro-1,4-dimethyl-7-(1-methylethenyl)-, [1S-(1.alpha.,4.alpha.,7.alpha.)]-;
Bicyclo[5.3.0]decane, 2-methylene-5-(1-methylvinyl)-8-methyl-; and,
Azulene, 1,2,3,5,6,7,8,8a-octahydro-1,4-dimethyl-7-(1-methylethenyl)-, [1S-(1.alpha.,7.alpha.,8a.beta.)]-.
and optionally a carrier, diluent or adjuvant.

Alternatively, the composition may comprise: ethanol; ethyl acetate; 1-Propanol, 2-methyl; Propanoic acid, 2-methyl-, methyl ester; 1-Butanol, 3-methyl; 1-Butanol, 2-methyl; and Propanoic acid, 2-methyl-, ethyl ester and optionally at least one of a carrier, diluent, surfactant, and adjuvant.

Further provided is a combination comprising (a) a first substance selected from the group consisting of (i) a substantially pure culture or whole cell broth comprising or (ii) cell fraction, supernatant, metabolite or volatile derived from the culture or *Muscodor* strain set forth above and (b) at least one of (i) a second substance, wherein said second substance is a chemical or biological pesticide and (ii) at least one of a carrier, diluent, surfactant, adjuvant. The combination may be a composition.

Also provided is a method for modulating pest infestation and/or phytopathogenic infection in a plant comprising applying to the plant and/or seeds, fruits, thereof and/or substrate, such as soil or hydroponic solution, used for growing said plant an amount of the compositions or artificial mixtures or combinations set forth above effective to modulate said pest infestation and/or phytopathogenic infection. The pest may be an insect pest, fungus, virus, bacteria, and nematode. Phytopathogenic infection may be caused by bacteria and/or fungus.

Also provided is a seed, particularly, a barley seed inoculated with said strain.

DETAILED DESCRIPTION

Figure 1:
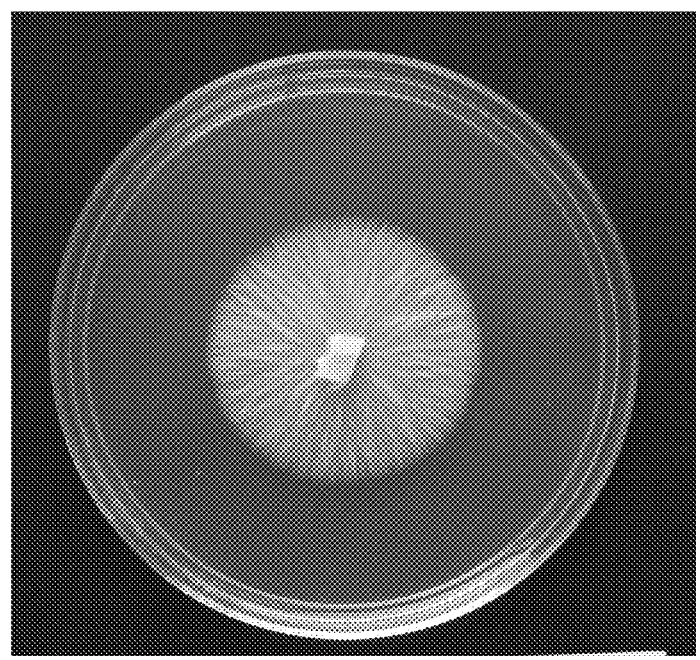
FIG. 1 shows a 20 day old culture of SA-13 growing on a potato dextrose agar (PDA) medium.

While the compositions and methods heretofore are susceptible to various modifications and alternative forms, exemplary embodiments will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Where a range of values is provided, it is understood that each intervening value, to the tenth of the unit of the lower limit unless the context clearly dictates otherwise, between the upper and lower limit of that range and any other stated or intervening value in that stated range, is included therein. Smaller ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

As defined herein, "derived from" means directly isolated or obtained from a particular source or alternatively having identifying characteristics of a substance or organism isolated or obtained from a particular source. In the event that the "source" is an organism, "derived from" means that it may be isolated or obtained from the organism itself or medium used to culture or grow said organism.

As defined herein, "whole broth culture" refers to a liquid culture containing both cells and media. If bacteria are grown on a plate the cells can be harvested in water or other liquid, whole culture.

The term "supernatant" refers to the liquid remaining when cells that are grown in broth or harvested in another liquid from an agar plate are removed by centrifugation, filtration, sedimentation, or other means well known in the art.

As defined herein, "filtrate" refers to liquid from a whole broth culture that has passed through a membrane.

As defined herein, "extract" refers to liquid substance removed from cells by a solvent (water, detergent, buffer, chemical such as acetone) and separated from the cells by centrifugation, filtration or other method.

As defined herein, "metabolite" or "volatile" refers to a compound, substance or by product of a fermentation of a microorganism, or supernatant, filtrate, or extract obtained from a microorganism.

As defined herein, an "isolated compound" is essentially free of other compounds or substances, e.g., at least about 20% pure, preferably at least about 40% pure, more preferably about 60% pure, even more preferably about 80% pure, most preferably about 90% pure, and even most preferably about 95% pure, as determined by analytical methods, including but not limited to chromatographic methods, electrophoretic methods.

A "carrier" as defined herein is an inert, organic or inorganic material, with which the active ingredient is mixed or formulated to facilitate its application to plant or other object to be treated, or its storage, transport and/or handling.

The term "modulate" as defined herein is used to mean to alter the amount of pest infestation or rate of spread of pest infestation.

The term "pest infestation" as defined herein, is the presence of a pest in an amount that causes a harmful effect including a disease or infection in a host population or emergence of an undesired weed in a growth system.

A "pesticide" as defined herein, is a substance derived from a biological product or chemical substance that increases mortality or inhibits the growth rate of plant pests and includes but is not limited to nematicides, insecticides, plant fungicides, plant bactericides, and plant viricides.

Methods of Production

As noted above, compounds, metabolites or volatiles may be obtained, are obtainable or derived from an organism having one or more identifying characteristics of the *Muscodor* strain or culture set forth above. The methods comprise cultivating these organisms and obtaining the compounds and/or compositions of the present invention by isolating these compounds from the culture of these organisms. In particular, the organisms are cultivated in nutrient medium using methods known in the art. The organisms may be cultivated by shake or non-shake cultivation, small scale or large scale fermentation (including but not limited to continuous, batch, fed-batch, or solid state fermentations) in laboratory or industrial fermentation apparatus performed in suitable medium and under conditions allowing cell growth or on solid substrates such as agar. The cultivation may take place in suitable nutrient medium comprising carbon and nitrogen sources and inorganic salts, using procedures known in the art. Suitable media are available or may be available from commercial sources or prepared according to published compositions. In a particular embodiment and as set forth in the examples, the *Muscodor* strain may be cultivated on agar media such as potato dextrose agar (PDA) (D. Ezra et al., 2004. Microbiology, 150:4023) or in various grain media such as barley grains by inoculating the grains with the PDA plugs grown with the strain.

After cultivation, a supernatant, filtrate, volatile and/or extract of or derived from said *Muscodor* strain (e.g., *Muscodor albus* SA-13) may be used in formulating a pesticidal composition.

Alternatively, after cultivation, the compounds, volatiles and/or metabolites may be extracted from the culture broth.

The extract may be fractionated by chromatography. Chromatographic fractions may be assayed for toxic activity against, for example, fungi *Fusarium* or nematodes, such as a J2 nematode of *Meloidogyne* spp. using methods known in the art. This process may be repeated one or more times using the same or different chromatographic methods.

Compositions

Compositions may comprise whole broth cultures, liquid or solid cultures, or suspensions of a *Muscodor* strain, specifically a *Muscodor* strain having at least one of the identifying characteristics of *Muscodor albus* SA-13 strain, as well as supernatant, filtrate and/or extract or one or more and more particularly a plurality of (i) metabolites, (ii) isolated compounds or (iii) volatiles derived from *Muscodor albus* SA-13 strain of the foregoing which in particular have pesticidal and particularly fungicidal and/or nematicidal activity.

The compositions set forth above can be formulated in any manner. Non-limiting formulation examples include but are not limited to Dried grains such as barley, corn, rye, rice, and wheat, Emulsifiable concentrates (EC), Wettable powders (WP), Soluble liquids (SL), Aerosols, Ultra-low volume concentrate solutions (ULV), Soluble powders (SP), Microencapsulation, Water dispersed granules (WDG), Flowables (FL), Microemulsions (ME), Nano-emulsions (NE), etc. In any formulation described herein, percent of the active ingredient is within a range of 0.01% to 99.99%.

The compositions may be in the form of a liquid, gel or solid. A solid composition can be prepared by soaking a solid carrier in a solution of active ingredient(s) and drying the suspension under mild conditions, such as evaporation at room temperature or vacuum evaporation at 65° C. or lower. A solid composition can also be dried grains grown with the said strain. The composition may additionally comprise a surfactant to be used for the purpose of emulsification, dispersion, wetting, spreading, integration, disintegration control, stabilization of active ingredients, and improvement of fluidity or rust inhibition. In a particular embodiment, the surfactant is a non-phytotoxic non-ionic surfactant which preferably belongs to EPA List 4B. In another particular embodiment, the nonionic surfactant is polyoxyethylene (20) monolaurate. The concentration of surfactants may range between 0.1-35% of the total formulation, preferred range is 5-25%. The choice of dispersing and emulsifying agents, such as non-ionic, anionic, amphoteric and cationic dispersing and emulsifying agents, and the amount employed is determined by the nature of the composition and the ability of the agent to facilitate the dispersion of the compositions of the present invention.

The composition set forth above may be combined with another microorganism and/or pesticide (e.g., nematicide, bactericide, fungicide, insecticide). The microorganism may include but is not limited to an agent derived from *Bacillus* spp., *Paecilomyces* spp., *Pasteuria* spp. *Pseudomonas* spp., *Brevabacillus* spp., *Lecanicillium* spp., non-*Ampelomyces* spp., *Pseudozyma* spp., *Streptomyces* spp, *Burkholderia* spp, *Trichoderma* spp, *Gliocladium* spp. or other *Muscodor* strains. Alternatively, the agent may be a natural oil or oil-product having nematicidal, fungicidal, bactericidal and/or insecticidal activity (e.g., paraffinic oil, tea tree oil, lemongrass oil, clove oil, cinnamon oil, citrus oil, rosemary oil, pyrethrum).

Furthermore, the pesticide may be a single site anti-fungal agent which may include but is not limited to benzimidazole, a demethylation inhibitor (DMI) (e.g., imidazole, piperazine, pyrimidine, triazole), morpholine, hydroxypyrimidine, anilinopyrimidine, phosphorothiolate, quinone outside inhibitor, quinoline, dicarboximide, carboximide, phenylamide, anilinopyrimidine, phenylpyrrole, aromatic hydrocarbon, cinnamic acid, hydroxyanilide, antibiotic, polyoxin, acylamine, phthalimide, benzenoid (xylylalanine), a demethylation inhibitor selected from the group consisting of imidazole, piperazine, pyrimidine and triazole (e.g., bitertanol, myclobutanil, penconazole, propiconazole, triadimefon, bromuconazole, cyproconazole, diniconazole, fenbuconazole, hexaconazole, tebuconazole, tetraconazole), myclobutanil, and a quinone outside inhibitor (e.g., strobilurin). The strobilurin may include but is not limited to azoxystrobin, kresoxim-methoyl or trifloxystrobin. In yet another particular embodiment, the anti-fungal agent is a quinone, e.g., quinoxyfen (5,7-dichloro-4-quinolyl 4-fluorophenyl ether). The anti-fungal agent may also be derived from a *Reynoutria* extract.

The fungicide can also be a multi-site non-inorganic, chemical fungicide selected from the group consisting of chloronitrile, quinoxaline, sulphamide, phosphonate, phosphite, dithiocarbamate, chloralkythios, phenylpyridinamine, and cyano-acetamide oxime.

As noted above, the composition may further comprise a nematicide. This nematicide may include but is not limited to chemicals such as organophosphates, carbamates, and fumigants, and microbial products such as avermectin, *Myrothecium* spp., Biome (*Bacillus firmus*), *Pasteuria* spp., *Paecilomyces* spp., and organic products such as saponins and plant oils.

In the case that the composition is applied to a seed, the composition may be applied to the seed as one or more coats prior to planting the seed using one or more seed coating agents including, but are not limited to, ethylene glycol, polyethylene glycol, chitosan, carboxymethyl chitosan, peat moss, resins and waxes or chemical fungicides or bactericides with either single site, multisite or unknown mode of action using methods known in the art.

The composition may be coated on to a conventional seed as noted above. In a particular embodiment, the compostions set forth above may be coated on a barly seed. The coated barley seed may further comprise protein based ingredients such as milk, whey protein, high protein based flour from e.g., rice or wheat to enhance thestorage life of said seeds. Alternatively, the composition may be coated on a genetically modified seed such as Liberty Link (Bayer CropScience), Roundup Ready seeds (Monsanto), or other herbicide resistant seed, and/or seeds engineered to be insect resistant, or seeds that are "pyrimaded" with more than one genes for herbicide, disease, and insect resistance or other stress, such as drough, cold, salt resistance traits.

Uses

As noted above, the compositions set forth above may be applied using methods known in the art. Specifically, these compositions may be applied to and around plants or plant parts. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include, but are not limited to, harvested material, and vegetative and generative propagation material, for example cuttings, tubers, rhizomes, offshoots and seeds.

Plants that may be treated include but are not limited to: (A) Major edible food crops, which include but are not limited to (1) Cereals African rice, barley, durum wheat, einkorn wheat, emmer wheat, finger millet, foxtail millet, hairy crabgrass, Indian barnyard millet, Japanese barnyard millet, maize, nance, oat, pearl millet, proso millet, rice, rye, sorghum, *Sorghum* spp., rye, spelt wheat); (2) Fruits (e.g., abiu, acerola, achacha, African mangosteen, alpine currant, ambarella, American gooseberry, American persimmon, apple, apricot, arazá, Asian palmyra palm, Asian pear, atemoya, Australian desert raisin, avocado, azarole, babaco, bael, banana, Barbados gooseberry, bergamot, betel nut, bignay, bilberry, bilimbi, binjai, biriba, bitter orange, black chokeberry, black mulberry, black sapote, blackberry, blueberried honeysuckle, borojo, breadfruit, murmese grape, button mangosteen, cacao, calamondin, canistel, cantaloupe, cape gooseberry, cashew nut, cassabanana, cempedak, charichuelo, cherimoya, cherry, cherry of the Rio Grande, cherry plum, Chinese hawthorn, Chinese white pear, chokeberry, citron, cocona, coconut, cocoplum, coffee, coffee *Arabica*, coffee *robusta*, Costa Rica pitahaya, currants, custard apple, date, date-plum, dog rose, dragonfruit, durian, elderberry, elephant apple, Ethiopian eggplant, European nettle tree, European wild apple, feijoa, fig, gac, genipapo, giant granadilla, gooseberry, goumi, grape, grapefruit, great *morinda*, greengage, guava, hardy kiwi, hog plum, horned melon, horse mango, Indian fig, Indian jujube, jabuticaba, jackberry, jackfruit, Japanese persimmon, Japanese wineberry, jocote, jujube, kaffir lime, karanda, kei apple, kepel apple, key lime, kitembilla, kiwi fruit, korlan, kubal vine, kuwini mango, kwai muk, langsat, large cranberry, lemon, Liberian coffee, longan, loquat, lychee, malay apple, mamey sapote, mammee apple, mango, mangosteen, maprang, marang, medlar, melon, Mirabelle plum, miracle fruit, monkey jack, moriche palm, mountain *papaya*, mountain soursop, mulberry, naranjilla, natal plum, northern highbush blueberry, olive, otaheite gooseberry, oval kumquat, *papaya*, para guava, passion fruit, pawpaw, peach, peach-palm, pear, pepino, pineapple, pitomba *Eugenia luschnathiana*, pitomba talisia *esculenta*, plantain, plum, pomegranate, pomelo, pulasan, purple chokeberry, quince, rambutan, ramontchi, raspberry, red chokeberry, red currant, red mulberry, red-fruited strawberry guava, rhubarb, rose apple, roselle, safou, salak, salmonberry, santol, sapodilla, satsuma, seagrape, soncoya, sour cherry, soursop, Spanish lime, Spanish tamarind, star apple, starfruit, strawberry, strawberry guava, strawberry tree, sugar apple, Surinam cherry, sweet briar, sweet granadilla, sweet lime, tamarillo, tamarind, tangerine, tomatillo, tucuma palm, *Vaccinium* spp., velvet apple, wampee, watermelon, watery rose apple, wax apple, white currant, white mulberry, white sapote, white star apple, wolfberry (*Lyceum barbarum, L.chinense*), yellow mombin, yellow pitaya, yellow-fruited strawberry, guava, (3) Vegetables (e.g., ackee, agate, air potato, *Amaranthus* spp., American groundnut, antroewa, armenian cucumber, arracacha, arrowleaf elephant ear, arrowroot, artichoke, ash gourd, asparagus, avocado, azuki bean, bambara groundnut, bamboo, banana, Barbados gooseberry, beet, beet root, bitter gourd, bitter vetch, bitterleaf, black mustard, black radish, black salsify, blanched celery, breadfruit, broad bean, broccoli, Brussels sprout, Buck's horn plantain, buttercup squash, butternut squash, cabbage, caigua, calabash, caraway seeds, carob, carrot, cassabanana, cassava, catjang, cauliflower, celeriac, celery, celtuce, chard, chayote, chickpea, chicory, chilacayote, chili pepper (*Capsicum annuum, C. baccatum, C. chinense, C. frutescens, C. pubescens*), Chinese cabbage, Chinese water chestnut, Chinese yam, chives, chufa sedge, cole crops, common bean, common purslane, corn salad, cowpea, cress, cucumber, cushaw pumpkin, drumstick tree, eddoe, eggplant, elephant foot yam, elephant garlic, endive, enset, Ethiopian eggplant, Florence fennel, fluted gourd, gac, garden rocket, garlic, geocarpa groundnut, Good King Henry, grass pea, groundnut, guar bean, horse gram, horseradish, hyacinth bean, ice plant, Indian fig, Indian spinach, ivy gourd, Jerusalem artichoke, jacamar, jute, kale, kohlrabi, konjac, kurrat, leek, lentil, lettuce, Lima bean, lotus, luffa, maca, maize, mangel-wurzel, mashua, moso bamboo, moth bean, mung bean, napa cabbage, neem, oca, okra, Oldham's bamboo, olive, onion, parsnip, pea, pigeon pea, plantain, pointed gourd, potato, pumpkins, squashes, *quinoa*, radish, rapeseed, red amaranth, rhubarb, ribbed gourd, rice bean, root parsley, runner bean, rutabaga, sago palm, salsify, scallion, sea kale, shallot, snake gourd, snow pea, sorrel, soybean, spilanthes, spinach, spinach beet, sweet potato, taro, tarwi, teasle gourd, tepary bean, tinda, tomato, tuberous pea, turnip, turnip-rooted chervil, urad bean, water caltrop *trapa bicornis*, water caltrop *trapa natans*, water morning slory, watercress, welsh onion, west African okra, west Indian gherkin, white goosefoot, white yam, winged bean, winter purslane, yacón, yam, yard-long bean, zucchinietables); (4) Food crops (e.g., abiu, acerola, achacha, ackee, African mangosteen, African rice, agate, air potato, alpine currant, *Amaranthus* app., Ambarrella, American gooseberry, American groundnut, American persimmon, antroewa, apple, apricot, arazá, Armenian cucumber, arracacha, arrowleaf elephant ear, arrowroot, artichoke, ash gourd, Asian palmyra palm, Asian pear, asparagus, atemoya, Australian desert raisin, avocado, azarole, azuki bean, babaco, bael, bambara groundnut, bamboo, banana, barbados gooseberry, barley, beet, beetroot, bergamot, *betel* nut, bignay, bilberry, bilimbi, binjai, biriba, bitter gourd, bitter orange, bitter vetch, bitterleaf, black chokeberry, black currant, black mulberry, black mustard, black radish, black salsify, black sapote, blackberry, blanched celery, blue-berried honeysuckle, borojó, breadfruit, broad bean, broccoli, Brussels sprout, Buck's horn plantain, buckwheat, Burmese grape, buttercup squash, butternut squash, button mangosteen, cabbage, cacao, caigua, calabash, calamondin, canistel, cantaloupe, cape gooseberry, caraway seeds, carob, carrot, cashew nut, cassava, catjang, cauliflower, celeriac, celery, celtuce, cempedak, chard, charichuelo, chayote, cherimoya, cherry, cherry of the Rio Grande, cherry plum, chickpea, chicory, chilacayote, chili pepper (*Capsicum annuum, C. baccatum, C. chinense, C. frutescens, C. pubescens*), Chinese cabbage, Chinese hawthorn, Chinese water chestnut, Chinese white pear, Chinese yam, chives, chokeberry, chufa sedge, citron, cocona, coconut, cocoplum, coffee, coffee (*Arabica* and *Robusta* types), cole crops, common bean, common purslane, corn salad, Costa Rica pitahaya, cowpea, cress, cucumber, currants, cushaw pumpkin, custard apple, date, date-plum, dog rose, dragonfruit, drumstick tree, durian, *durum* wheat, eddoe, eggplant, einkorn wheat, elderberry, elephant apple, elephant foot yam, elephant garlic, emmer wheat, endive, enset, Ethiopian eggplant, European nettle tree, European wild apple, feijoa, fig, finger millet, Florence fennel, fluted gourd, foxtail millet, gac, garden rocket, garlic, genipapo, geocarpa groundnut, giant granadilla, good king henry, gooseberry, goumi, grape, grapefruit, grass pea, great *morinda*, greengage, groundnut, grumichama, guar bean, guava, hairy crabgrass, hardy kiwi, hog plum, horned melon, horse gram, horse mango, horseradish, hyacinth bean, ice-plant, Indian barnyard millet, Indian fig, Indian jujube, Indian spinach, ivy gourd, jabuticaba, jackalberry, jackfruit, jambul, Japanese barnyard millet, Japanese persimmon, Japanese wineberry, Jerusalem artichoke, jocote, jujube, jute, kaffir lime, kale, karanda, kei apple, kepel apple, key lime, kitembilla, kiwifruit, kohlrabi, konjac, korlan, kubal vine, kurrat, kuwini mango, kwai muk, langsat, large cranberry, leek, lemon, lentil, lettuce, Liberian coffee, lima bean, longan, loquat, lotus, luffa, lychee, maca, maize, malay apple, mamey saptoe, mammee apple, mangel-wurzel, mango, mangosteen, maprang, marang, mashua, medlar, melon, Mirabelle plum, miracle fruit, monk fruit, monkey jack, moriche palm, moso bamboo, moth bean, mountain *papaya*, mountain soursop, mulberry, mung bean, mushrooms, nance, napa cabbage, naranjilla, natal plum, neem, northern highbush blueberry, oat, oca, oil palm, okra, old man's bamboo, olive, onion, orange, otaheite gooseberry, oval kumquat, *papaya*, para guava, parsnip, passionfruit, pawpaw, pea, peach, peach-palm, pear, pearl millet, pepino, pigeon pea, pineapple, Pitomba (*Eugenia luschnathiana, Talisia esculenta*), plantain, plum, pointed gourd, pomegranate, pomelo, potato, proso millet, pulasan, pumpkins and squashes, purple chokeberry, quince, *quinoa*, radish, rambutan, ramontchi, rapeseed, raspberry, red amaranth, red chokeberry, red currant, red mulberry, red-fruited strawberry guava, rhubarb, ribbed gourd, rice, rice bean, root parsley, rose apple, roselle, runner bean, rutabaga, rye, safou, sago palm, salak, salmonberry, salsify, santol, sapodilla, Satsuma, scallion, sea kale, seagrape, shallot, snake gourd, snow pea, soncoya, sorghum, *Sorghum* spp., sorrel, sour cherry, soursop, soybean, Spanish lime, Spanish tamarind, spelt wheat, spilanthes, spinach, spinach beet, star apple, starfruit, strawberry, strawberry guava, strawberry tree, sugar apple, sugar beet, sugarcane, surinam cherry, sweet briar, sweet granadilla, sweet lime, sweet potato, tamarillo, tamarind, tangerine, taro, tarwi, teasle gourd, *tef*, tepary bean, tinda, tomatillo, tomato, tuberous pea, tucuma palm, turnip, turnip-rooted chervil, urad bean, *Vaccinium* spp., velvet apple, wampee, water caltrop (*Trapa bicornis, T. natans*), water morning glory, watercress, watermelon, watery rose apple, wax apple, welsh onion, west African okra, west Indian gherkin, wheat, white currant, white goosefoot, white mulberry, white sapote, white star apple, white yam, winged bean, winter purslane, wolfberry (*Lycium barbarum, L. chinense*), yacón, yam, yangmei, yard-long bean, yellow mombin, yellow pitaya, yellow-fruited strawberry guava, zucchini; (B) Other edible crops, which includes but is not limited to (1) Herbs (e.g., *Absinthium*, alexanders, basil, bay laurel, *betel* nut, camomile, chervil, chili pepper (*Capsicum annuum, C. baccatum, C. chinense, C. frutescens, C. pubescens*), chili peppers, chives, cicely, common rue, common thyme, coriander, cress, culantro, curly leaf parsley, dill, epazote, fennel, flat leaf parsley, *ginseng*, gray *santolina*, herb hyssop, holy basil, hop, jasmine, kaffir lime, lavender, lemon balm, lemon basil, lemon grass, lovage, marjoram, mint, oregano, parsley, peppermint, *perilla*, pot marigold, rooibos, rosemary, sage, shiny-leaft buckthorn, sorrel, spearmint, summer savory, tarragon, Thai basil, valerian, watercress, wild *betel*, winter savory, yerba maté); (2) Spices (e.g., ajowan, allspice, anise, bay laurel, black cardamom, black mustard, black pepper, caper, caraway seeds, cardamom, chili pepper (*Capsicum annuum, C. baccatum, C. chinense, C. frutescens, C. pubescens*), chili peppers, cinnamon, clove, common juniper, coriander, cumin, fennel, fenugreek, garlic, ginger, kaffir lime, liquorice, nutmeg, oregano, pandan, parsley, saffron, star anise, turmeric, vanilla, white mustard); (2) Medicinal plants (e.g., *absinthium*, alfalfa, aloe vera, anise, artichoke, basil, bay laurel, *betel* leaf, *betel* nut, bilberry, black cardamom, black mustard, black pepper, blue gum, borojo, chamomile, caper, cardamom, castor bean, chili peppers, Chinese yam, chives, cola nut, common jasmine, common lavender, common myrrh, common rue, cilantro, cumin, dill, dog rose, epazote, fennel, fenugreek, gac, garlic, ginger, gray *santolina*, gum Arabic, herb hyssop, holy basil, horseradish, incense tree, lavender, lemon grass, liquorice, lovage, marijuana, marjoram, monk fruit, neem, opium, oregano, peppermint, pot marigold, quinine, red *acacia*, red currant, rooibos, safflower, sage, shiny-leaf buckthorn, sorrel, spilanthes, star anise, tarragon, tea, turmeric, valerian, velvet bean, watercress, white mustard, white sapote, wild *betel*, wolfberry (*Lycium barbarum, L. chinense*), yerba maté); (3) Stimulants (e.g., *betel* leaf, *betel* nut, cacao, chili pepper (*Capsicum annuum, C. baccatum, C. chinense, C. frutescens, C. pubescens*), chili peppers, coffee, coffee (*Arabica, Robusta*), cola nut, khat, Liberian coffee, tea, tobacco, wild *betel*, yerba maté); (4) Nuts (e.g., almond, *betel* nut, Brazil nut, cashew nut, chestnut, Chinese water chestnut, coconut, cola nut, common walnut, groundnut, hazelnut, Japanese stone oak, macadamia, nutmeg, paradise nut, pecan nut, pistachio nut, walnut); (5) Edible seeds (e.g., black pepper, Brazil nut, chilacayote, cola nut, fluted gourd, lotus, opium, *quinoa*, sesame, sunflower, water caltrop (*Trapa bicornis, T. natans*)); (6) Vegetable oils (e.g., black mustard, camelina, castor bean, coconut, cotton, linseed, maize, neem, *Niger* seed, oil palm, olive, opium, rapeseed, safflower, sesame, soybean, sunflower, tung tree, turnip); (7) Sugar crops (e.g., Asian palmyra palm, silver date palm, sorghum, sugar beet, sugarcane); (8) Pseudocereals (e.g., *Amaranthus* spp., buckwheat, *quinoa*, red amaranth); (9) Aphrodisiacs (e.g., borojo, celery, durian, garden rocket, *ginseng*, maca, red *acacia*, velvet bean); (C) Non food categories, including but not limited to (1) forage and dodder crops (e.g., agate, alfalfa, beet, broad bean, camelina, catjang, grass pea, guar bean, horse gram, Indian barnyard millet, Japanese barnyard millet, *lespedeza*, lupine, maize, mangel-wurzel, mulberry, *Niger* seed, rapeseed, rice bean, rye); (2) Fiber crops (e.g., coconut, cotton, fique, hemp, henequen, jute, kapok, kenaf, linseed, manila hemp, New Zealand flax, ramie, roselle, sisal, white mulberry); (3) Energy crops (e.g., blue gum, camelina, cassava, maize, rapeseed, sorghum, soybean, Sudan grass, sugar beet, sugarcane, wheat); (4) Alcohol production (e.g., barley, plum, potato, sugarcane, wheat, sorghum); (5) Dye crops (e.g., chay root, henna, indigo, old fustic, safflower, saffron, turmeric); (6) Essential oils (e.g., allspice, bergamot, bitter orange, blue gum, camomile, citronella, clove, common jasmine, common juniper, common lavender, common myrrh, field mint, freesia, gray *santolina*, herb hyssop, holy basil, incense tree, jasmine, lavender, lemon, marigold, mint, orange, peppermint, pot marigold, spearmint, ylang-ylang tree); (6) Green manures (e.g., alfalfa, clover, lacy Phacelia, sunn hemp, trefoil, velvet bean, vetch); (7) Erosion prevention (e.g., bamboo, cocoplum); (8) Soil improvement (e.g., lupine, vetch); (9) Cover crops (e.g., Alfalfa, lacy Phacelia, radish); (10) Botanical pesticides (e.g., jicama, marigold, neem, pyrethrum); (11) Cut flowers (e.g., carnation, *chrysanthemum*, daffodil, dahlia, freesia, *gerbera*, marigold, rose, sunflower, tulip); (12) Ornamental plants (e.g., African mangosteen, aloe vera, alpine currant, aster, black chokeberry, breadfruit, calamondin, carnation, cassabanana, castor bean, cherry plum, chokeberry, *chrysanthemum*, cocoplum, common lavender, *crocus*, daffodil, dahlia, freesia, *gerbera*, hyacinth, Japanese stone oak, Jasmine, lacy Phacelia, lotus, lupine, marigold, New Zealand flax, opium, purple chokeberry, ramie, red chokeberry, rose, sunflower, tulip, white mulberry); (D) Trees which include but are not limited to abelia, almond, apple, apricot, arborvitae nigra American, arborvitae, ash, aspen, azalea, bald cypress, beautush, beech, birch, black tupelo, blackberry, blueberry, boxwood, buckeye, butterfly bush, butternut, *camellia, catalpa*, cedar, cherry, chestnut, coffee tree, crab trees, crabapple, crape myrtle, cypress, dogwood, Douglas fir, ebony, elder American, elm, fir, forsythia, ginkgo, goldenraintree, hackberry, hawthorn, hazelnut, hemlock, hickory, holly, honey locust, horse chestnut, *hydrangea*, juniper, lilac, linden, *magnolia*, maple, mock orange, mountain ash, oak, olive, peach, pear, pecan, pine, pistachio, plane tree, plum, poplar, pivet, raspberry, redbud, red cedar, redwood, *rhododendron*, rose-of-Sharon, *sassafras, sequoia*, serviceberry, smoke tree, soapberry, sourwood, spruce, strawberry tree, sweet shrub, sycamore, tulip tree, ciborium, walnut, weasel, willow, winterberry, witch-hazel, *zelkova*; (E) Turf which includes but is not limited to Kentucky bluegrass, tall fescue, Bermuda grass, *zoysia* grass, perennial ryegrass, fine fescues (e.g.; creeping red, chewings, hard, or sheep fescue).

Treatment of the plants and plant parts with the compositions set forth above may be carried out directly or by allowing the compositions to act on their surroundings, habitat or storage space by, for example, immersion, coating, dipping, spraying, evaporation, fogging, scattering, painting on, injecting.

The compositions may also be applied to the soil using methods known in the art. These include but are not limited to (a) drip irrigation or chemigation; (b) soil incorporation; (c) seed treatment.

The compositions, cultures, supernatants, metabolites and pesticidal compounds set forth above may be used as pesticides and in particular, may be used as insecticides, nematicides, fungicides and bactericides, alone or in combination with one or more pesticidal substances set forth above and applied to plants, plant parts, substrate for growing plants or seeds set forth above.

The compositions, cultures, supernatants, metabolites and pesticidal compounds set forth above may be combined with other enhancing compounds for the said compositions such as, but not limited to, amino acids, chitosan, chitin, starch, hormones, minerals, synergistic microbes to increase efficacy and promote benefits to plants.

Specifically, nematodes that may be controlled using the method set forth above include but are not limited to parasitic nematodes such as root-knot, reniform, cyst, and lesion nematodes, including but not limited to *Aphelenchoides* spp., *Belonolaimus* spp., *Bursaphalenchus* spp., *Criconema* spp. *Globodera* spp., *Meloidogyne* spp., *Tylenchorhynchus* spp., *Helicotylenchus* spp., *Heterodera* spp., *Hoplolaimus* spp., *Pratylenchus* spp., *Rotylenchulus* spp., *Trichodorus* spp., and *Xiphinema* spp. In particular, the parasitic nematodes may include but are not limited to seed gall nematodes (*Afrina wevelli*), bentgrass nematodes (*Anguina agrostis*), shoot gall nematodes (*Anguina* spp.), seed gall nematodes (*Anguina* spp., *A. amsinckiae*, *A. balsamophila*; *A. tritici*), fescue leaf gall nematodes (*A. graminis*), ear-cockle (or wheat gall) nematodes (*Anguina tritici*), bud and leaf (or foliar) nematodes (*Aphelenchoides* spp., *A. subtenuis*), begonia leaf (or fern, or spring crimp, or strawberry foliar, or strawberry nematodes, or summer dwarf) nematodes (*A. fragariae*), fern nematodes (*A. olesistus*), rice nematodes (*A. oryzae*), currant nematodes (*A. ribes*), black currant (or chrysanthemum) nematodes (*A. ritzemabosi*), chrysanthemum foliar or leaf nematodes (*A. ritzemabosi*), rice white-tip (or spring dwarf, or strawberry bud) nematodes (*A. besseyi*), fungus-feeding (mushroom) nematodes (*Aphelenchoides* compositicola), *Atalodera* spp. (*Atalodera lonicerae*, *Atalodera ucri*), spine nematodes (*Bakernema variabile*), sting nematodes (*Belonolaimus* spp., *B. gracilis*, *B. longicaudatus*), pine wood nematodes (*Bursaphalenchus* spp., *B. xylophilus*, *B. mucronatus*), sessile nematodes (*Cacopaurus* spp., *C. epacris*, *C. pestis*), amaranth cyst nematodes (*Cactodera amaranthi*), birch cyst nematodes (*C. betulae*), cactus cyst nematodes (*C.cacti*), estonian cyst nematodes (*C. estonica*), Thorne's cyst nematodes (*C. thornei*), knotweed cyst nematodes (*C. weissi*), ring nematodes (*Criconema* spp.), spine nematodes (*Criconema* spp., *C. civellae*, *C. decalineatum*, *C.spinalineatum*), ring nematodes (*Criconemella axeste*, *C. curvata*, *C. macrodora*, *C. parva*), ring nematodes (*Criconemoides* spp., *C. citri*, *C. simile*), spine nematodes (*Crossonema fimbriatum*), eucalypt cystoid nematodes (*Cryphodera eucalypti*), bud, stem and bulb nematodes (*Ditylenchus* spp., *D. angustus*, *D. dipsaci*, *D. destructor*, *D. intermedius*), Mushroom spawn nematodes (*D. myceliophagus*), awl nematodes (*Dolichodorus* spp., *D. heterocephalus*, *D. heterocephalous*), spear nematodes (*Dorylaimus* spp.), stunt nematodes (*Geocenamus superbus*), cyst nematodes (*Globodera* spp.), yarrow cyst nematodes (*G. achilleae*), milfoil cyst nematodes (*G. millefolii*), apple cyst nematodes (*G. mali*), white cyst potato nematodes (*G. pallida*), golden nematodes (*G. rostochiensis*), tobacco cyst nematodes (*G. tabacum*), Osborne's cyst nematodes (*G. tabacum solanacearum*), horsenettle cyst nematodes (*G. tabacum virginiae*), pin nematodes (*Gracilacus* spp., *G. idalimus*), spiral nematodes (*Helicotylenchus* spp., *H. africanus*, *H. digonicus*, *H. dihystera*, *H. erythrinae*, *H. multicinctus*, *H. paragirus*, *H. pseudorobustus*, *H. solani*, *H. spicaudatus*), sheathoid nematodes (*Hemicriconemoides* spp., *H. biformis*, *H. californianus*, *H. chitwoodi*, *H. floridensis*, *H. wessoni*), sheath nematodes (*Hemicycliophora* spp., *H. arenaria*, *H. biosphaera*, *H. megalodiscus*, *H. parvana*, *H. poranga*, *H. sheri*, *H. similis*, *H. striatula*), cyst nematodes (*Heterodera* spp.), almond cyst nematodes (*H. amygdali*), oat (or cereal) cyst nematodes (*H. avenae*), Cajanus (or pigeon pea) cyst nematodes (*H. cajani*), Bermuda grass (or heart-shaped, or Valentine) cyst nematodes (*H. cardiolata*), carrot cyst nematodes (*H. carotae*), cabbage cyst nematodes or *brassica* root eelworm (*H.cruciferae*), nutgrass (or sedge) cyst nematodes (*H. cyperi*), Japanese cyst nematodes (*H. elachista*), fig (or *ficus*, or rubber) cyst nematodes (*H. fici*), galeopsis cyst nematodes (*H. galeopsidis*), soybean cyst nematodes (*H. glycines*), alfalfa root (or pea cyst) nematodes (*H. goettingiana*), buckwheat cyst nematodes (*H. graduni*), barley cyst nematodes (*H. hordecalis*), hop cyst nematodes (*H. humuli*), Mediterranean cereal (or wheat) cyst nematodes (*H. latipons*), lespedeza cyst nematodes (*H. lespedezae*), Kansas cyst nematodes (*H. longicolla*), cereals root eelworm or oat cyst nematodes (*H. major*), grass cyst nematodes (*H. mani*), lucerne cyst nematodes (*H. medicaginis*), cyperus (or motha) cyst nematodes (*Heterodera mothi*), rice cyst nematodes (*H. oryzae*), Amu-Darya (or camel thorn cyst) nematodes (*H. oxiana*), dock cyst nematodes (*H. rosii*), rumex cyst nemtodes (*H. rumicis*), sugar beet cyst nematodes (*H. schachtii*), willow cyst nematodes (*H. salixophila*), knawel cyst nematodes (*H. scleranthii*), sowthistle cyst nematodes (*H. sonchophila*), tadzhik cyst nematodes (*H. tadshikistanica*), turkmen cyst nematodes (*H. turcomanica*), clover cyst nematodes (*H. trifolii*), nettle cyst nematodes (*H. urticae*), ustinov cyst nematodes (*H. ustinovi*), cowpea cyst nematodes (*H. vigni*), corn cyst nematodes (*H. zeae*), rice root nematodes (*Hirschmanniella* spp., *H. belli*, *H. caudacrena*, *H. gracilis*, *H.oryzae*), lance nematodes (*Hoplolaimus* spp.), Columbia nematodes (*H. columbus*), Cobb's lance nematodes (*H. galeatus*), crown-headed lance nematodes (*H. tylenchiformis*), pseudo root-knot nematodes (*Hypsoperine graminis*), needle nematodes (*Longidorus* spp., *L. africanus*, *L. sylphus*), ring nematodes (*Macroposthonia* (=*Mesocriconema*) *xenoplax*), cystoid nematodes (*Meloidodera* spp.), pine cystoid nematodes (*M. floridensis*), tadzhik cystoid nematodes (*M. tadshikistanica*), cystoid body nematodes (*Meloidoderita* spp.), stunt nematodes (*Merlinius* spp., *M. brevidens*, *M. conicus*, *M. grandis*, *M. microdorus*), root-knot nematodes (*Meloidogyne* spp., *M. acronea*, *M. arenaria*, *M.artiellia*, *M. brevicauda*, *M. camelliae*, *M. carolinensis*, *M. chitwoodi*, *M. exigua*, *M. graminicola*, *M. hapla*, *M. hispanica*, *M. incognita*, *M. incognita acrita*, *M. indica*, *M. inornata*, *M. javanica*, *M. kikuyuensis*, *M. konaensis*, *M. mali*, *M. microtyla*, *M. naasi*, *M. ovalis*, *M. platani*, *M. querciana*, *M. sasseri*, *M. tadshikistanica*, *M. thamesi*), knapweed nematodes (*Mesoanguina picridis*), Douglas fir nematodes (*Nacobbodera chitwoodi*), false root-knot nematodes (*Nacobbus aberrans*, *N. batatiformis*, *N. dorsalis*), sour paste nematodes (*Panagrellus redivivus*), beer nematodes (*P. silusiae*), needle nematodes (*Paralongidorus microlaimus*), spiral nematodes (*Pararotylenchus* spp.), stubby-root nematodes (*Paratrichodorus allius*, *P. minor*, *P. porosus*, *P. renifer*), pin nematodes (*Paratylenchus* spp., *P. baldaccii*, *P. bukowinensis*, *P. curvitatus*, *P. dianthus*, *P. elachistus*, *P. hamatus*, *P. holdemani*, *P. italiensis*, *P. lepidus*, *P. nanus*, *P. neoamplycephalus*, *P. similis*), lesion (or meadow) nematodes (*Pratylenchus* spp., *P. alleni*, *P. brachyurus*, *P. coffeae*, *P. convallariae*, *P. crenatus*, *P. flakkensis*, *P. goodeyi*, *P. hexincisus*, *P. leiocephalus*, *P. minyus*, *P. musicola*, *P. neglectus*, *P.penetrans*, *P. pratensis*, *P. scribneri*, *P. thornei*, *P. vulnus*, *P. zeae*), stem gall nematodes (*Pterotylenchus cecidogenus*), grass cyst nematodes (*Punctodera punctate*), stunt nematodes (*Quinisulcius acutus*, *Q. capitatus*), burrowing nematodes (*Radopholus* spp.), banana-root nematodes (*R. similis*), rice-root nematodes (*R. oryzae*), red ring (or coconut, or cocopalm) nematodes (*Rhadinaphelenchus cocophilus*), reniform nematodes (*Rotylenchulus* spp., *R. reniformis, R. parvus*), spiral nematodes (*Rotylenchus* spp., *R. buxophilus, R. christiei, R. robustus*), Thorne's lance nematodes (*R. uniformis*), Sarisodera hydrophylla, spiral nematodes (*Scutellonema* spp., *S. blaberum, S. brachyurum, S. bradys, S. clathricaudatum, S. christiei, S. conicephalum*), grass root-gall nematodes (*Subanguina radicicola*), round cystoid nematodes (*Thecaverrmiculatus andinus*), stubby-root nematodes (*Trichodorus* spp., *T. christiei, T. kurumeensis, T. pachydermis, T. primitivus*), vinegar eels (or nematodes) (*Turbatrix aceti*), stunt (or stylet) nematodes (*Tylenchorhynchus* spp., *T. agri, T. annulatus, T. aspericutis, T. claytoni, T.ebriensis, T. elegans, T. golden, T.graciliformis, T. martini, T. mashhoodi, T. microconus, T. nudus, T. oleraceae, T. penniseti, T. punensis*), citrus nematodes (*Tylenchulus semipenetrans*), dagger nematodes (*Xiphinema* spp., *X. americanum, X. bakeri, X. brasiliense, X. brevicolle, X. chambersi, X. coxi, X. diversicaudatum X. index, X. insigne, X. nigeriense, X. radicicola, X. setariae, X. vulgarae, X. vuittenezi*). In a particular embodiment nematodes controlled are member of the *Meloidogyne* spp, particularly, *M. hapla* or *M. incognita*.

Phytopathogenic insects controlled by the method set forth above include but are not limited to non-Culicidae larvae insects from the order (a) Lepidoptera, for example, *Acleris* spp., *Adoxophyes* spp., *Aegeria* spp., *Agrotis* spp., *Alabama argillaceae, Amylois* spp., *Anticarsia gemmatalis, Archips* spp., *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora gossypiella, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.; (b) Coleoptera, for example, *Agriotes* spp., *Alphitobius* sp., *Anomola* spp., e.g., *Anomala orientalis, Anthonomus* spp., *Atomaria linearis, Chaetocnema tibialis, Cosmopolites* spp., *Curculio* spp., *Cyclocephala* spp., e.g., *Cyclocephala lurida, Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Otiorhynchus sulcatus, Phlyctinus* spp., *Popillia* spp., e.g., *Popilla japonica, Psylliodes* spp., *Rhizopertha* spp., e.g., *Rhizotrogus majalis, Sitophilus* spp., *Sitotroga* spp., *Tenebrio* spp., *Tribolium* spp. and *Trogoderma* spp.; (c) Orthoptera, for example, *Blatta* spp., *Blattella* spp., *Gryllotalpa* spp., *Leucophaea maderae, Locusta* spp., *Periplaneta* spp. and *Schistocerca* spp.; (d) Isoptera, for example, *Reticulitermes* spp.; (e) Psocoptera, for example, *Liposcelis* spp.; (f) Anoplura, for example, *Haematopinus* spp., *Linognathus* spp., *Pediculus* spp., *Pemphigus* spp. and *Phylloxera* spp.; (g) Mallophaga, for example, *Damalinea* spp. and *Trichodectes* spp.; (h) Thysanoptera, for example, *Frankliniella* spp., *Hercinotnrips* spp., *Taeniothrips* spp., *Thrips palmi, Thrips tabaci* and *Scirtothrips aurantii*; (i) Hemiptera, for example, *Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp. and *Tniatoma* spp.; *Aleurothrixus floccosus, Aleyrodes brassicae, Aonidiella* spp., *Aphididae, Aphis* spp., *Aspidiotus* spp., *Bactericera* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lecanium corni, Lepidosaphes* spp., *Macrosiphus* spp., *Myzus* spp., *Nephotettix* spp., *Nilaparvata* spp., *Paratoria* spp., *Pemphigus* spp., *Planococcus* spp., *Pseudaulacaspis* spp., *Pseudococcus* spp., *Psylla* spp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Triozidae* spp., *Trioza erytreae* and *Unaspis citri*; (j) Hymenoptera, for example, Acromyrmex, *Atta* spp., *Cephus* spp., *Diprion* spp., *Diprionidae, Gilpinia polytoma, Hoplocampa* spp., *Lasius* spp., *Monomorium pharaonis, Neodiprion* spp., *Solenopsis* spp. and *Vespa* spp.; (k) Diptera, for example, *Aedes* spp., *Antherigona soccata, Bibio hortulanus, Calliphora erythrocephala, Ceratitis* spp., *Chrysomyia* spp., *Cuterebra* spp., *Dacus* spp., *Delia* spp., *Delia radicum, Drosophila* spp., e.g., *Drosophila suzukii; Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp.; (l) Siphonaptera, for example, *Ceratophyllus* spp. and *Xenopsylla cheopis*; (m) from the order Thysanura, for example, *Lepisma saccharina*.

Phytopathogenic bacteria includes but is not limited to *Agrobacterium* spp. (e.g., *Agrobacterium tumefaciens*); *Erwinia, Pantoea, Pectobacterium, Serratia, S. marcescens, Acidovorax, Pseudomonas, Ralstonia, Rhizobacter, Rhizomonas, Xanthomonas, Xylophilus, Agrobacterium, Rhizobium, Bacillus, Clostridium, Arthrobacter, Clavibacter, Curtobacterium, Leifsonia, Rhodococcus, Streptomyces, Xanthomonas* spp. (*Xanthomonas axonopodis, Xanthomonas oryzae pv. oryzae, Xanthomonas vesicatoria*). In a particular embodiment, phytopathogenic bacteria includes but is not limited to *Clavibacter* spp., *Xanthomonas* spp., *Pseudomonas* (e.g., *Pseudomonas syringae*), *Pectobacterium* (e.g., *Pectobacterium carotovorum*).

Phytopathogenic fungi includes but is not limited to *Alternaria* spp. (e.g., *Alternaria alternate, Alternaria solani*); *Aphanomyces* spp. (e.g., *Aphanomyces euteiches*); *Aspergillus* spp. (e.g., *Aspergillus niger, Aspergillus fumigatus*); *Athelia* spp. (e.g., *Athelia rolfsii*); *Aureobasidium* spp. (e.g., *Aureobasidium pullulans*); *Bipolaris* spp. (e.g. *Bipolaris zeicola, Bipolaris maydis*); *Botrytis* spp. (e.g., *Botrytis cinerea*); *Calonectria* spp. (e.g., *Calonectria kyotensis*); *Cephalosporium* spp. (e.g., *Cephalosporium maydis*); *Cercospora* spp. (e.g., *Cercospora medicaginis, Cercospora sojina, Colletotrichum coccodes, Colletotrichum fragariae, Colletotrichum graminicola*); *Coniella* spp. (e.g., *Coniella diplodiella*); *Coprinopsis* spp. (e.g., *Coprinopsis psychromorbida*); *Corynespora* spp. (e.g., *Corynespora cassiicola; Curvularia* spp. (e.g., *Curvularia pallescens*); *Cylindrocladium* spp. (e.g., *Cylindrocladium crotalariae*); *Diplocarpon* spp. (e.g., *Diplocarpon earlianum*); *Diplodia* spp. (e.g., *Diplodia gossyina*); *Epicoccum* spp. (e.g., *Epicoccum nigrum*); *Erysiphe* spp. (*Erysiphe cichoracearum*); *Fusarium* spp. (e.g., *Fusarium graminearum, Fusarium oxysporum f.sp. fragariae, Fusarium oxysporum f.sp. tuberosi, Fusarium proliferatum* var. *proliferatum*,

*Fusarium solani, Fusarium verticillioides*); *Ganoderma* spp. (e.g., *Ganoderma boninense*); *Geotrichum* spp. (e.g., *Geotrichum candidum*); *Glomerella* spp. (e.g., *Glomerella tucumanensis*); *Guignardia* spp. (e.g., *Guignardia bidwellii*); *Kabatiella* spp. (e.g., *Kabatiella zeae*); *Leptosphaerulina* spp. (e.g., *Leptosphaerulina briosiana*); *Leptotrochila* spp. (e.g., *Leptotrochila medicaginis*); *Macrophomina* spp. (e.g., *Macrophomina phaseolina*); *Magnaporthe* spp. (e.g., *Magnaporthe grisea, Magnaporthe oryzae*); *Microsphaera* spp. (e.g., *Microsphaera manshurica*); *Monilinia* spp. (e.g., *Monilinia fructicola*); *Mucor* spp.; *Mycosphaerella* spp. (e.g., *Mycosphaerella jijiensis, Mycosphaerella fragariae*); *Nigrospora* spp. (e.g., *Nigrospora oryzae*); *Ophiostoma* spp. (e.g., *Ophiostoma ulmi*); *Penicillium* spp.; *Peronospora* spp. (e.g., *Peronospora manshurica*); *Phakopsora* (e.g., *Phakopsora pachyrhizi*); *Phoma* spp. (e.g., *Phoma foveata, Phoma medicaginis*); *Phomopsis* spp (e.g. *Phomopsis longicolla*); *Phytophthora* spp. (e.g., *Phytophthora cinnamomi, Phytophthora erythroseptica, Phytophthora fragariae, Phytophthora infestans, Phytophthora medicaginis, Phytophthora megasperma, Phytophthora palmivora*); *Podosphaera* (e.g., *Podosphaera leucotricha*); *Pseudopeziza* spp. (e.g., *Pseudopeziza medicaginis*); *Puccinia* spp. (e.g., *Puccinia graminis* subsp. *tritici* (UG99), *Puccinia striiformis, Puccinia recodita, Puccinia sorghi*); *Pyricularia* spp. (*Pyricularia grisea, Pyricularia oryzae*); *Pythium* spp. (e.g., *Pythium ultimum*); *Rhizoctonia* spp. (e.g., *Rhizoctonia solani, Rhizoctonia zeae*); *Rosellinia* spp., *Sclerotinia* spp. (e.g., *Sclerotinia minor; Sclerotinia sclerotiorum, Sclerotinina trifoliorum*); *Sclerotium* spp. (e.g., *Sclerotium rolfsii*); *Septoria* spp. (e.g., *Septoria glycines, Septoria lycoperski*); *Setomelanomma* spp. (e.g., *Setomelanomma turcica*); *Sphaerotheca* spp. (e.g., *Sphaerotheca macularis*); *Spongospora* spp. (e.g., *Spongospora subterranean*); *Stemphylium* spp., *Synchytrium* spp. (e.g., *Synchytrium endobioticum*), *Verticillium* spp. (e.g., *Verticillium albo-atrum, Verticillium dahliae*). In a particular embodiment, the fungus is a member of the *Botrytis* spp. (e.g., *Botrytis cinerea*), *Sclerotinia* spp. (*Sclerotinia minor*), *Sclerotium* spp. (e.g., *Sclerotium rolfsii*), *Macrophomina* spp. (e.g., *Macrophomina phaseolina*), *Verticillium* spp. (e.g., *Verticillium dahliae*), *Fusarium* spp. (e.g., *Fusarium oxysporum* f.sp. *fragariae*), *Rhizoctonia* spp. (e.g., *Rhizoctonia solani*), *Pythium* spp. (e.g., *Pythium ultimum*).

EXAMPLES

The example below is presented to describe preferred embodiments and utilities of the invention and is not meant to limit the invention unless otherwise stated in the claims appended hereto.

Example 1

Isolation of *Muscodor albus* Strain SA-13

The *Muscodor albus* strain SA-13 was originally obtained from the host plant *Prosopis grandulosa* in southern Africa.

The host plant, *Prosopis*, is a tall shrub or tree of 3-9 m; foliage deciduous; spines axillary, uninodal, 1-4.5 cm long, mostly solitary, sometimes very few, or solitary and geminate alternately on different nodes of the same twig. Leaves glabrous, uni- or bijugate; petiole (with rachis when extant) 2-15 cm long; pinnae 6-17 cm long; leaflets 6 to 17 pairs, ca 7-18 mm distant on the rachis, linear or oblong, obtuse, glabrous, subcoriaceous, prominently veined below, costa frequently of lighter color, (1.5-) 2-6.3 cm long×1.5-4.5 mm broad, 5 to 15 times as long as broad. Racemes spiciform as usual, ca. 5-14 cm long, multiflorous; petals 2.5-3.5 mm long; ovary stipilate, villous. Legume straight, 8-20 cm long×0.7-1.3 cm broad, rarely subfalcate, compressed to subterete, submoniliform, glabrous, straw-yellow or tinged with violet, short-stiped, with strong, short, or elongate acumen, ca. 5-18-seeded; joints subquadrate to oval; seeds oblique to longitudinal.

It is native to southern USA (i.e. south-western Kansas, Oklahoma, New Mexico, Texas, Arizona, southern California and southern Nevada) and Mexico. This species is widely naturalized in Australia, but has a scattered distribution. It is present in many parts of Queensland and well as in northern Western Australia and south-western New South Wales. It is also naturalized overseas in southern Africa, western Asia (i.e. Saudi Arabia), the Indian Sub-continent (i.e. India and Pakistan), south-eastern Asia (i.e. Burma) and tropical Southern America.

Example 2

Morphological Characterization of *Muscodor albus* Strain SA-13

Figure 2:
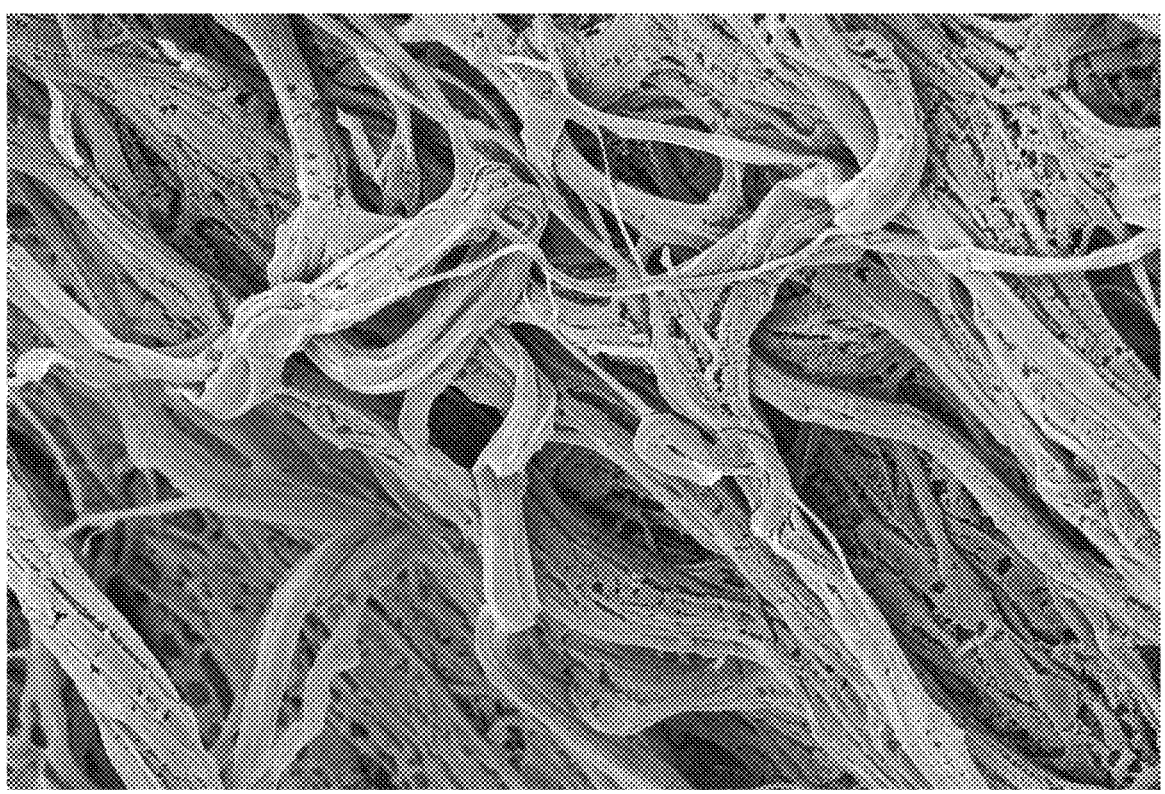
FIG. 2 shows a Scanning Electron Micrograph (SEM) of *Muscodor albus* as isolated from *Prosopis glandulosa* and particularly illustrates the intertwining hyphae.

Cultures of the organism appear whitish and have an overall greasy tone (FIG. 1). Under a stereoscopic microscope the growing hyphae have a spear-like appearance with little or no immediate branching patterns. The organism has never been observed to produce spores in culture or on tissues of its host plant. The mycelia hyphae are intertwined and rope like in appearance and have individual hyphal diameters ranging from 1-3 µl (FIG. 2). This characteristic is common in all *Muscodor* spp. (Strobel, G. A. 2006. Current Opinions in Microbiology. 9: 240-244; Strobel, G. A. 2012. Microbiology Today 39-2: 108-111 and Strobel, G. A. 2011. Phytochemistry Reviews 10:165-172).

Example 3

ITS Sequence Analysis

Phylogenetic analysis of SA-13 was carried out by the acquisition of the ITS-5.8 S ribosomal gene sequence. The fungus was grown on PDA for seven days and DNA templates were prepared by using the Prepman Ultra Sample Preparation Reagent according to the manufacturer's guidelines (Applied Biosystems, USA). The ITS regions of the fungus were amplified with the universal ITS primers ITS 1 (5'TCCGTAGGTGAACCTGCGG 3') (SEQ ID NO:1)) and ITS4 (5'TCCTCCGCTTATTGATATGC 3' (SEQ ID NO:2)) using the polymerase chain reaction (PCR). The PCR conditions used were as follows: initial denaturation at 94° C. for 3 min followed by 30 cycles of 94° C. for 15 sec., 50° C. for 30 sec., 72° C. for 45 sec., and a final extension at 72° C. for 5 min. The 50 µl reaction mixture contained 1×PCR buffer, 200 µM each dNTP, 1.5 mM MgCl$_2$, 10 pmol of each primer, 1-5 ng of extracted DNA and 2.5 U of Taq DNA polymerase. The amplified product (5 µl) was visualized on 1% (w/v) agarose gel to confirm the presence of a single amplified band. The amplified products were purified by Amicon Ultra columns (Millipore, USA) and 20-40 ng were used in a 10 µl sequencing reaction using the Big Dye Terminator sequencing kit (v. 3.1), with 2 pmoles of the forward or the reverse primer in the cycle sequencing reaction. Twenty cycles of 96° C. for 10 sec, 50° C. for 5 sec and 60° C. for 4 min were performed and the extension products were purified by ethanol precipitation, dissolved in 10 μl of HiDi Formamide, incubated at 95° C. for 1 min and loaded on ABI Prism 377 Genetic Analyzer (Perkin-Elmer, USA) for sequencing. All the reagents for sequencing were from Applied Biosystems, USA. The DNA sequence was aligned with the reference sequences in GenBank by BLASTN program as shown in Table 1 below.

TABLE 1

Comparison of *Muscodor albus* SA-13 strain rRNA with other *Muscodor* rRNAs

| Accession | Description | Max score | Total score | Query coverage | E value | Max ident |
|---|---|---|---|---|---|---|
| AF324336.1 | *Muscodor albus* internal transcribed spacer 1, partial sequence; 5.8S ribosomal RNA gene, complete sequence; and internal transcribed spacer 2, partial sequence | 1033 | 1033 | 100% | 0.0 | 100% |
| JX089321.1 | *Muscodor* sp. CMU-WR2 18S ribosomal RNA gene, partial sequence; internal transcribed spacer 1, 5.8S ribosomal RNA gene, and internal transcribed spacer 2, complete sequence; and 28S ribosomal RNA gene, partial sequence | 1027 | 1027 | 100% | 0.0 | 99% |
| AY927993.1 | *Muscodor albus* internal transcribed spacer 1, partial sequence; 5.8S ribosomal RNA gene, complete sequence; and internal transcribed spacer 2, partial sequence | 1024 | 1024 | 99% | 0.0 | 99% |
| JN426991.1 | *Muscodor* sp. AB-2011 18S ribosomal RNA gene, partial sequence; internal transcribed spacer 1, 5.8S ribosomal RNA gene, and internal transcribed spacer 2, complete sequence; and 28S ribosomal RNA gene, partial sequence | 1018 | 1018 | 99% | 0.0 | 99% |
| AY034665.1 | *Muscodor* sp. A3-5 18S ribosomal RNA gene, partial sequence; internal transcribed spacer 1, 5.8S ribosomal RNA gene and internal transcribed spacer 2, complete sequence; and 28S ribosomal RNA gene, partial sequence | 1014 | 1014 | 100% | 0.0 | 99% |
| GQ848369.1 | *Muscodor cinnamomi* strain CMU-Cib 461 internal transcribed spacer 1, partial sequence; 5.8S ribosomal RNA gene, complete sequence; and internal transcribed spacer 2, partial sequence | 1013 | 1013 | 100% | 0.0 | 99% |
| AY244622.1 | *Muscodor albus* 18S ribosomal RNA gene, partial sequence; internal transcribed spacer 1, 5.8S ribosomal RNA gene, and internal transcribed spacer 2, complete sequence; and 28S ribosomal RNA gene, partial sequence | 1011 | 1011 | 100% | 0.0 | 99% |
| EU977236.1 | Fungal endophyte sp. P912B internal transcribed spacer 1, partial sequence; 5.8S ribosomal RNA gene, complete sequence; and internal transcribed spacer 2, partial sequence | 1007 | 1007 | 98% | 0.0 | 99% |
| EU977187.1 | Fungal endophyte sp. P1509A internal transcribed spacer 1, partial sequence; 5.8S ribosomal RNA gene, complete sequence; and internal transcribed spacer 2, partial sequence | 1007 | 1007 | 98% | 0.0 | 99% |
| AY527048.1 | *Muscodor albus* strain GP 206 internal transcribed spacer 1, 5.8S ribosomal RNA gene, and internal transcribed spacer 2, complete sequence | 1007 | 1007 | 99% | 0.0 | 99% |
| AY527046.1 | *Muscodor albus* strain KN 27 internal transcribed spacer 1, 5.8S ribosomal RNA gene, and internal transcribed spacer 2, complete sequence | 1007 | 1007 | 99% | 0.0 | 99% |
| AY527045.1 | *Muscodor albus* strain TP 21 internal transcribed spacer 1, 5.8S ribosomal RNA gene, and internal transcribed spacer 2, complete sequence | 1007 | 1007 | 99% | 0.0 | 99% |
| AY527044.1 | *Muscodor albus* strain KN 26 internal transcribed spacer 1, 5.8S ribosomal RNA gene, and internal transcribed spacer 2, complete sequence | 1002 | 1002 | 99% | 0.0 | 99% |
| EU977281.1 | Fungal endophyte sp. P1907B internal transcribed spacer 1, partial sequence; 5.8S ribosomal RNA gene, complete sequence; and internal transcribed spacer 2, partial sequence | 998 | 998 | 97% | 0.0 | 99% |

TABLE 1-continued

Comparison of *Muscodor albus* SA-13 strain rRNA with other *Muscodor* rRNAs

| Accession | Description | Max score | Total score | Query coverage | E value | Max ident |
|---|---|---|---|---|---|---|
| JX089323.1 | *Muscodor* sp. CMU-MU3 18S ribosomal RNA gene, partial sequence; internal transcribed spacer 1, 5.8S ribosomal RNA gene, and internal transcribed spacer 2, complete sequence; and 28S ribosomal RNA gene, partial sequence | 996 | 996 | 98% | 0.0 | 99% |
| JQ760598.1 | *Sordariomycetes* sp. genotype 322 isolate FL0969 internal transcribed spacer 1, partial sequence; 5.8S ribosomal RNA gene and internal transcribed spacer 2, complete sequence; and 28S ribosomal RNA gene, partial sequence | 996 | 996 | 96% | 0.0 | 99% |
| HM034857.1 | *Muscodor albus* isolate 9-6 internal transcribed spacer 1, partial sequence; 5.8S ribosomal RNA gene, complete sequence; and internal transcribed spacer 2, partial sequence | 985 | 985 | 95% | 0.0 | 100% |
| AY527047.1 | *Muscodor albus* strain GP 115 internal transcribed spacer 1, 5.8S ribosomal RNA gene, and internal transcribed spacer 2, complete sequence | 985 | 985 | 99% | 0.0 | 99% |
| JQ760221.1 | *Sordariomycetes* sp. genotype 322 isolate FL0502 internal transcribed spacer 1, partial sequence; 5.8S ribosomal RNA gene and internal transcribed spacer 2, complete sequence; and 28S ribosomal RNA gene, partial sequence | 974 | 974 | 94% | 0.0 | 99% |
| GQ220337.1 | Fungal sp. ZH S13-1-2 internal transcribed spacer 1, partial sequence; 5.8S ribosomal RNA gene and internal transcribed spacer 2, complete sequence; and 28S ribosomal RNA gene, partial sequence | 965 | 965 | 93% | 0.0 | 100% |
| JQ760887.1 | *Sordariomycetes* sp. genotype 380 isolate FL1272 internal transcribed spacer 1, partial sequence; 5.8S ribosomal RNA gene and internal transcribed spacer 2, complete sequence; and 28S ribosomal RNA gene, partial sequence | 955 | 955 | 97% | 0.0 | 98% |
| GQ924909.1 | *Muscodor* sp. CMU20 18S ribosomal RNA gene, partial sequence; internal transcribed spacer 1, 5.8S ribosomal RNA gene, and internal transcribed spacer 2, complete sequence; and 28S ribosomal RNA gene, partial sequence | 955 | 955 | 93% | 0.0 | 99% |
| EU195297.1 | *Muscodor crispans* isolate B-23 internal transcribed spacer 1, partial sequence; 5.8S ribosomal RNA gene, complete sequence; and internal transcribed spacer 2, partial sequence | 955 | 955 | 92% | 0.0 | 100% |
| EF183509.1 | *Muscodor albus* isolate E-6 internal transcribed spacer 1, partial sequence; 5.8S ribosomal RNA gene, complete sequence; and internal transcribed spacer 2, partial sequence | 953 | 953 | 96% | 0.0 | 99% |
| JQ760423.1 | *Sordariomycetes* sp. genotype 380 isolate FL0763 internal transcribed spacer 1, partial sequence; 5.8S ribosomal RNA gene and internal transcribed spacer 2, complete sequence; and 28S ribosomal RNA gene, partial sequence >gb|JQ760617.1| *Sordariomycetes* sp. genotype 380 isolate FL0989 internal transcribed spacer 1, partial sequence; 5.8S ribosomal RNA gene and internal transcribed spacer 2, complete sequence; and 28S ribosomal RNA gene, partial sequence | 946 | 946 | 96% | 0.0 | 98% |
| EU977208.1 | Fungal endophyte sp. P913A internal transcribed spacer 1, partial sequence; 5.8S ribosomal RNA gene, complete sequence; and internal transcribed spacer 2, partial sequence | 937 | 937 | 91% | 0.0 | 99% |
| AY555731.1 | *Muscodor albus* strain GP 100 internal transcribed spacer 1, 5.8S ribosomal RNA gene, and internal transcribed spacer 2, complete sequence | 929 | 929 | 99% | 0.0 | 97% |

TABLE 1-continued

Comparison of *Muscodor albus* SA-13 strain rRNA with other *Muscodor* rRNAs

| Accession | Description | Max score | Total score | Query coverage | E value | Max ident |
|---|---|---|---|---|---|---|
| JN558830.1 | *Muscodor* sp. CMU462 18S ribosomal RNA gene, partial sequence; internal transcribed spacer 1, 5.8S ribosomal RNA gene, and internal transcribed spacer 2, complete sequence; and 28S ribosomal RNA gene, partial sequence | 909 | 909 | 96% | 0.0 | 97% |
| HM473081.1 | *Muscodor albus* strain CMU44 18S ribosomal RNA gene, partial sequence; internal transcribed spacer 1, 5.8S ribosomal RNA gene, and internal transcribed spacer 2, complete sequence; and 28S ribosomal RNA gene, partial sequence | 909 | 909 | 88% | 0.0 | 100% |
| JQ761048.1 | *Sordariomycetes* sp. genotype 475 isolate FL1438 internal transcribed spacer 1, partial sequence; 5.8S ribosomal RNA gene and internal transcribed spacer 2, complete sequence; and 28S ribosomal RNA gene, partial sequence | 874 | 874 | 96% | 0.0 | 96% |
| GU797134.1 | *Muscodor* sp. GBA internal transcribed spacer 1, partial sequence; 5.8S ribosomal RNA gene, complete sequence; and internal transcribed spacer 2, partial sequence | 874 | 874 | 84% | 0.0 | 100% |
| JQ409997.1 | *Muscodor* sp. 1CCSTITD internal transcribed spacer 1, partial sequence; 5.8S ribosomal RNA gene, complete sequence; and internal transcribed spacer 2, partial sequence | 784 | 784 | 81% | 0.0 | 97% |
| JQ409998.1 | *Muscodor* sp. 2CCSTITD internal transcribed spacer 1, partial sequence; 5.8S ribosomal RNA gene, complete sequence; and internal transcribed spacer 2, partial sequence | 773 | 773 | 81% | 0.0 | 98% |
| JQ409999.1 | *Muscodor* sp. 6610CMSTITBRT internal transcribed spacer 1, partial sequence; 5.8S ribosomal RNA gene, complete sequence; and internal transcribed spacer 2, partial sequence | 706 | 706 | 81% | 0.0 | 94% |
| FJ917287.1 | *Muscodor yucatanensis* strain B110 18S ribosomal RNA gene, partial sequence; internal transcribed spacer 1, 5.8S ribosomal RNA gene, and internal transcribed spacer 2, complete sequence; and 28S ribosomal RNA gene, partial sequence | 702 | 702 | 99% | 0.0 | 90% |
| FJ664551.1 | *Muscodor* sp. WG-2009a internal transcribed spacer 1, 5.8S ribosomal RNA gene, and internal transcribed spacer 2, complete sequence | 693 | 693 | 99% | 0.0 | 90% |
| JX089322.1 | *Muscodor* sp. CMU-M2 18S ribosomal RNA gene, partial sequence; internal transcribed spacer 1, 5.8S ribosomal RNA gene, and internal transcribed spacer 2, complete sequence; and 28S ribosomal RNA gene, partial sequence | 680 | 680 | 99% | 0.0 | 90% |
| FJ612989.1 | Fungal sp. ARIZ B342 18S ribosomal RNA gene, partial sequence; internal transcribed spacer 1, 5.8S ribosomal RNA gene, and internal transcribed spacer 2, complete sequence; and 28S ribosomal RNA gene, partial sequence | 680 | 680 | 99% | 0.0 | 90% |
| JQ760849.1 | *Sordariomycetes* sp. genotype 264 isolate FL1234 internal transcribed spacer 1, partial sequence; 5.8S ribosomal RNA gene and internal transcribed spacer 2, complete sequence; and 28S ribosomal RNA gene, partial sequence | 671 | 671 | 96% | 0.0 | 90% |
| JQ760604.1 | *Sordariomycetes* sp. genotype 264 isolate FL0975 internal transcribed spacer 1, partial sequence; 5.8S ribosomal RNA gene and internal transcribed spacer 2, complete sequence; and 28S ribosomal RNA gene, partial sequence | 671 | 671 | 96% | 0.0 | 90% |

TABLE 1-continued

Comparison of *Muscodor albus* SA-13 strain rRNA with other *Muscodor* rRNAs

| Accession | Description | Max score | Total score | Query coverage | E value | Max ident |
|---|---|---|---|---|---|---|
| JQ760574.1 | *Sordariomycetes* sp. genotype 264 isolate FL0942 internal transcribed spacer 1, partial sequence; 5.8S ribosomal RNA gene and internal transcribed spacer 2, complete sequence; and 28S ribosomal RNA gene, partial sequence | 671 | 671 | 96% | 0.0 | 90% |
| EU687035.1 | Fungal endophyte isolate 2161 18S ribosomal RNA gene, partial sequence; internal transcribed spacer 1, 5.8S ribosomal RNA gene, and internal transcribed spacer 2, complete sequence; and 28S ribosomal RNA gene, partial sequence >gb|JQ760022.1| *Sordariomycetes* sp. genotype 264 isolate FL0230 internal transcribed spacer 1, partial sequence; 5.8S ribosomal RNA gene and internal transcribed spacer 2, complete sequence; and 28S ribosomal RNA gene, partial sequence >gb|JQ760240.1| *Sordariomycetes* sp. genotype 264 isolate FL0523 internal transcribed spacer 1, partial sequence; 5.8S ribosomal RNA gene and internal transcribed spacer 2, complete sequence; and 28S ribosomal RNA gene, partial sequence >gb|JQ760530.1| *Sordariomycetes* sp. genotype 264 isolate FL0894 internal transcribed spacer 1, partial sequence; 5.8S ribosomal RNA gene and internal transcribed spacer 2, complete sequence; and 28S ribosomal RNA gene, partial sequence >gb|JQ760814.1| *Sordariomycetes* sp. genotype 264 isolate FL1198 internal transcribed spacer 1, partial sequence; 5.8S ribosomal RNA gene and internal transcribed spacer 2, complete sequence; and 28S ribosomal RNA gene, partial sequence >gb|JQ760833.1| *Sordariomycetes* sp. genotype 264 isolate FL1217 internal transcribed spacer 1, partial sequence; 5.8S ribosomal RNA gene and internal transcribed spacer 2, complete sequence; and 28S ribosomal RNA gene, partial sequence >gb|JQ760851.1| *Sordariomycetes* sp. genotype 264 isolate FL1236 internal transcribed spacer 1, partial sequence; 5.8S ribosomal RNA gene and internal transcribed spacer 2, complete sequence; and 28S ribosomal RNA gene, partial sequence >gb|JQ760944.1| *Sordariomycetes* sp. genotype 264 isolate FL1326 internal transcribed spacer 1, partial sequence; 5.8S ribosomal RNA gene and internal transcribed spacer 2, complete sequence; and 28S ribosomal RNA gene, partial sequence | 671 | 671 | 96% | 0.0 | 90% |
| AY100022.1 | *Muscodor vitigenus* internal transcribed spacer 1, 5.8S ribosomal RNA gene and internal transcribed spacer 2, complete sequence; and 28S ribosomal RNA gene, partial sequence | 671 | 671 | 99% | 0.0 | 89% |
| JQ761995.1 | *Sordariomycetes* sp. genotype 524 isolate NC1638 internal transcribed spacer 1, partial sequence; 5.8S ribosomal RNA gene and internal transcribed spacer 2, complete sequence; and 28S ribosomal RNA gene, partial sequence | 669 | 669 | 95% | 0.0 | 90% |
| JQ761355.1 | *Sordariomycetes* sp. genotype 524 isolate NC0319 internal transcribed spacer 1, partial sequence; 5.8S ribosomal RNA gene and internal transcribed spacer 2, complete sequence; and 28S ribosomal RNA gene, partial sequence | 669 | 669 | 95% | 0.0 | 90% |

TABLE 1-continued

Comparison of *Muscodor albus* SA-13 strain rRNA with other *Muscodor* rRNAs

| Accession | Description | Max score | Total score | Query coverage | E value | Max ident |
|---|---|---|---|---|---|---|
| JQ761313.1 | *Sordariomycetes* sp. genotype 514 isolate NC0275 internal transcribed spacer 1, partial sequence; 5.8S ribosomal RNA gene and internal transcribed spacer 2, complete sequence; and 28S ribosomal RNA gene, partial sequence | 669 | 669 | 95% | 0.0 | 90% |
| HM999898.1 | *Muscodor* sp. E6710b 18S ribosomal RNA gene, partial sequence; internal transcribed spacer 1, 5.8S ribosomal RNA gene, and internal transcribed spacer 2, complete sequence; and 28S ribosomal RNA gene, partial sequence | 669 | 669 | 96% | 0.0 | 90% |
| EU686946.1 | Fungal endophyte isolate 1730 18S ribosomal RNA gene, partial sequence; internal transcribed spacer 1, 5.8S ribosomal RNA gene, and internal transcribed spacer 2, complete sequence; and 28S ribosomal RNA gene, partial sequence | 667 | 667 | 94% | 0.0 | 90% |
| JQ761395.1 | *Sordariomycetes* sp. genotype 531 isolate NC0363 internal transcribed spacer 1, partial sequence; 5.8S ribosomal RNA gene and internal transcribed spacer 2, complete sequence; and 28S ribosomal RNA gene, partial sequence | 665 | 665 | 96% | 0.0 | 90% |
| JQ760860.1 | *Sordariomycetes* sp. genotype 264 isolate FL1245 internal transcribed spacer 1, partial sequence; 5.8S ribosomal RNA gene and internal transcribed spacer 2, complete sequence; and 28S ribosomal RNA gene, partial sequence | 665 | 665 | 96% | 0.0 | 90% |
| JQ760698.1 | *Sordariomycetes* sp. genotype 264 isolate FL1075 internal transcribed spacer 1, partial sequence; 5.8S ribosomal RNA gene and internal transcribed spacer 2, complete sequence; and 28S ribosomal RNA gene, partial sequence | 665 | 665 | 96% | 0.0 | 90% |
| JQ760692.1 | *Sordariomycetes* sp. genotype 264 isolate FL1069 internal transcribed spacer 1, partial sequence; 5.8S ribosomal RNA gene and internal transcribed spacer 2, complete sequence; and 28S ribosomal RNA gene, partial sequence | 665 | 665 | 96% | 0.0 | 90% |
| JQ760567.1 | *Sordariomycetes* sp. genotype 264 isolate FL0935 internal transcribed spacer 1, partial sequence; 5.8S ribosomal RNA gene and internal transcribed spacer 2, complete sequence; and 28S ribosomal RNA gene, partial sequence | 665 | 665 | 96% | 0.0 | 90% |
| JQ760541.1 | *Sordariomycetes* sp. genotype 264 isolate FL0905 internal transcribed spacer 1, partial sequence; 5.8S ribosomal RNA gene and internal transcribed spacer 2, complete sequence; and 28S ribosomal RNA gene, partial sequence | 665 | 665 | 95% | 0.0 | 90% |
| JQ760537.1 | *Sordariomycetes* sp. genotype 264 isolate FL0901 internal transcribed spacer 1, partial sequence; 5.8S ribosomal RNA gene and internal transcribed spacer 2, complete sequence; and 28S ribosomal RNA gene, partial sequence | 665 | 665 | 96% | 0.0 | 90% |

Figure 3:
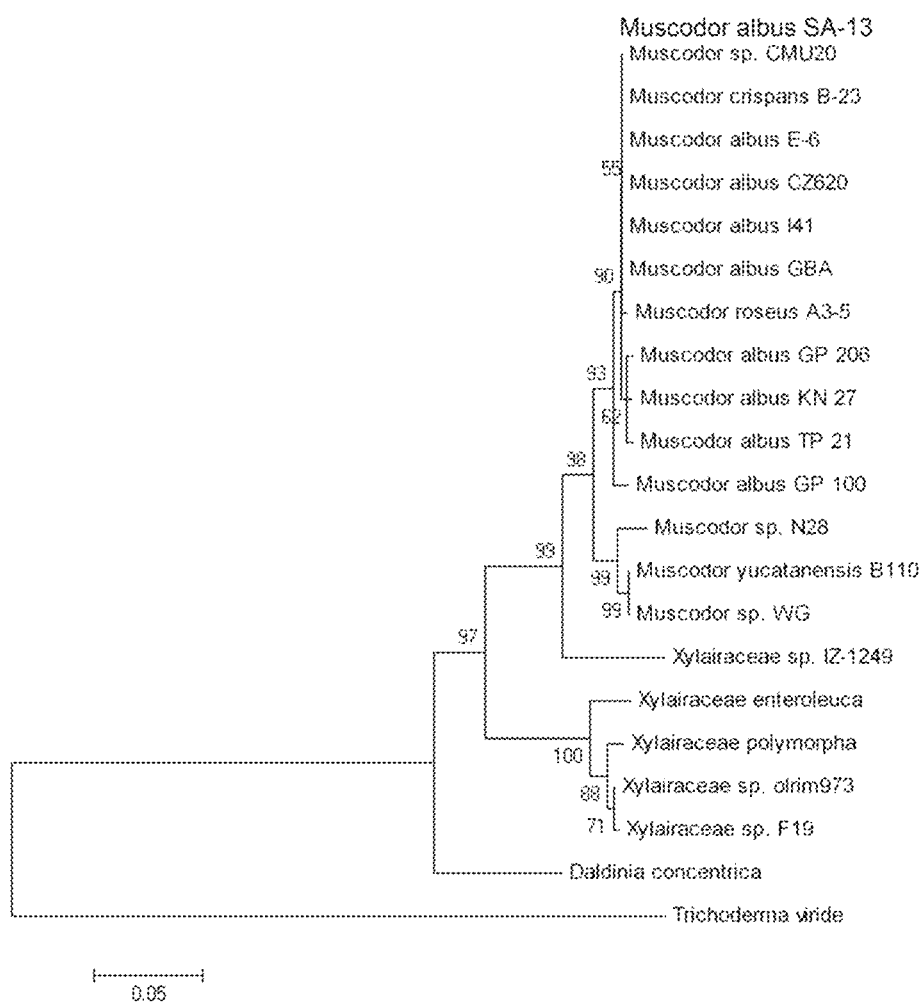
FIG. 3 shows a phylogenetic tree showing genetic relationships among *Muscodor* spp. The isolate SA-13 is included in the list in the upper right side of the diagram.

The ITS rDNA sequence of the strain SA-13 has a high similarity with other isolates of *M. albus* and *M. crispans*. And it has 100% identity with many other isolates of *Muscodor albus* including the CZ 620 isolate, *M. crispans* and others shown in FIG. 3.

Example 4

Analysis of Volatiles Produced by *Muscodor albus* CZ 620 and SA-13

Prior to use, the fiber (50/30 μm DVB/CAR/PDMS, Stableflex 24Ga, Supelco Cat. #57328-U) was conditioned via the injection port at 250° C. for 30 min under a flow of helium gas. Sampling of the gases produced by *Muscodor* grown on barley grains was done by exposing the fiber to the gas space region of the culturing flask through a small hole of the culturing flask's lid for 30 min at ambient temperature. The syringe was then inserted into the split less injection port of an Agilent 7890A gas chromatograph containing a 20 m×0.18 mm I.D. DB-VRX column with a film thickness of 1.0 μm. The column was temperature programmed as follows: 45° C. for 3 min followed to 170° C. at 15° C./min and then from 170° C. to 225° C. at 35° C. and then hold at 225° C. for 5 min. Ultra high purity Helium was used as carrier gas and ran at a rate of 55 cm/sec (1.5 mL/min) and initial column head pressure of 29 psi. A 15 sec injection time was used to desorb VOCs trapped on the fiber into the GC. The gas chromatograph was interfaced to an Agilent 5975C inert XL MSD with Triple-Axis Detector. The Mass Spectrometer was set to scan at a rate of 2.3 scans per second over a mass range of 16-500 amu. Data acquisition and processing were done using the Agilent ChemStation software. Initial identification of the unknowns produced by *Muscodor albus* SA-13 was made through library match with available spectra database from NIST.

Study 1. SPME-GCMS Analysis of Volatiles Produced by *Muscodor albus* CZ 620 Grown on Barley Grains.

Figure 4:
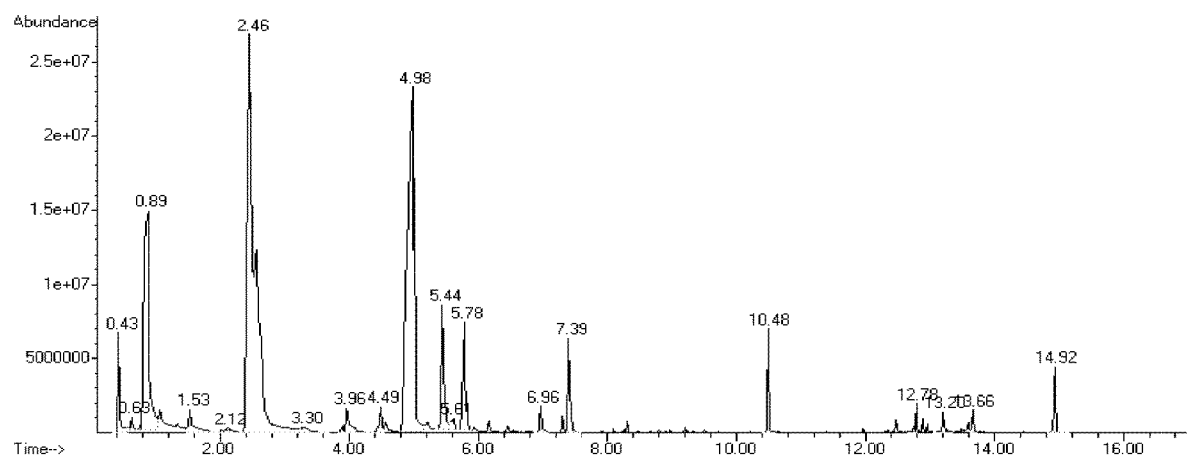
FIG. 4 shows a chromatographic representation of VOCs produced by *Muscodor albus* CZ 620 as analyzed using SPME-GCMS.

*Muscodor albus* CZ 620 was grown on barley grains for 17 days and the volatile organic compounds (VOCs) produced were sampled and analyzed. A chromatographic representation of the analysis is shown in FIG. 4. An identification of the VOCs produced by *Muscodor albus* CZ 620 was made via a library match with the available NIST database. The results are tabulated in Table 1.

TABLE 1

SPME-GCMS analysis of volatiles produced by the *Muscodor albus* CZ 620 strain grown on barley grains.

| Entry | RT (min) | Possible Compound ID |
|---|---|---|
| 1 | 0.76 | Ethanol |
| 2 | 1.53 | Propanol |
| 3 | 2.47 | 2-Butanone, 4-hydroxy- |
| 4 | 2.53 | Ethyl Acetate |
| 5 | 3.97 | Propanoic acid, 2-methyl-, methyl ester |
| 6 | 4.48 | 2-Butanone, 3-hydroxy- |
| 7 | 4.58 | n-Propyl acetate |
| 8 | 4.91 | 1-Butanol, 3-methyl- |
| 9 | 5.01 | 1-Butanol, 2-methyl- |
| 10 | 5.44 | Propanoic acid, 2-methyl-, ethyl ester |
| 11 | 5.62 | Propanoic acid, 2-methyl |
| 12 | 5.78 | Butanoic acid, 2-methyl-, methyl ester |
| 13 | 6.16 | Butanoic acid, ethyl ester |
| 14 | 6.96 | Butanoic acid, 2-methyl-, ethyl ester |
| 15 | 7.3 | 2-Butenoic acid, 2-methyl-, methyl ester |
| 16 | 7.39 | 1-Butanol, 3-methyl-, acetate |

TABLE 1-continued

SPME-GCMS analysis of volatiles produced by the *Muscodor albus* CZ 620 strain grown on barley grains.

| Entry | RT (min) | Possible Compound ID |
|---|---|---|
| 17 | 8.3 | Ethyl tiglate |
| 18 | 10.48 | Phenylethyl Alcohol |
| 19 | 13.19 | 1H-3a,7-methanoazulene, 2,3,4,7,8,8a-hexahydro-3,6,8,8-tetramethyl-, [3R-(3R(3,alpha.,3a.beta.,7.beta.,8a.alpha.)]- |
| 20 | 14.92 | Azulene, 1,2,3,5,6,7,8,8a-octahydro-1,4-dimethyl-7-(1-methylethenyl)-, (1S-(1.alpha.,7.alpha.,8a.beta.)]- |

Study 2. SPME-GCMS Analysis of VOCs Produced by *Muscodor albus* SA-13 Strain Grown on Barley Grains.

Figure 5:
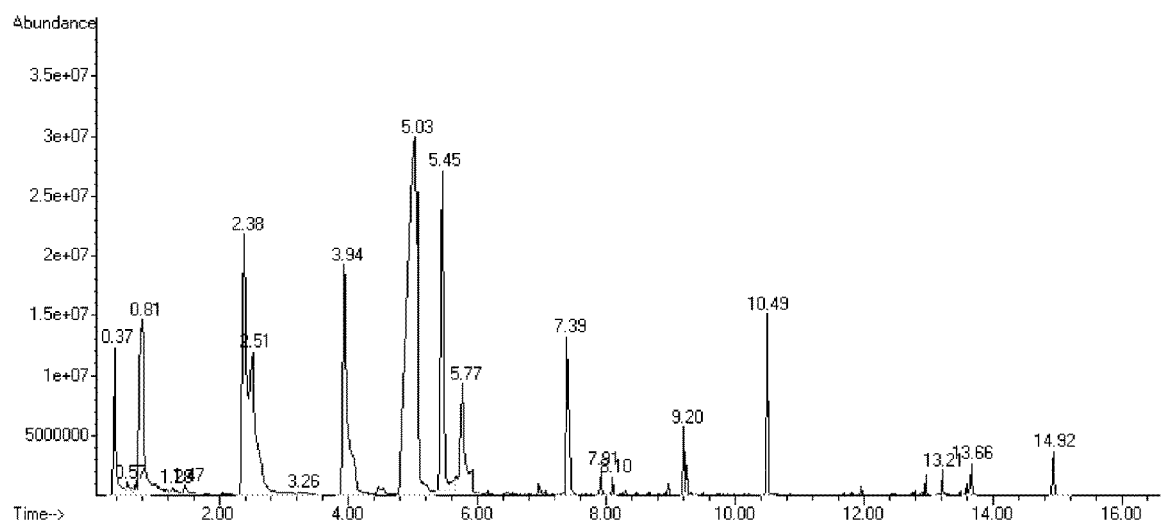
FIG. 5 shows a chromatographic representation of VOCs produced by *Muscodor albus* SA-13 as analyzed using SPME-GCMS.

*Muscodor albus* SA-13 was grown on barley grains for 10 days and the VOCs produced were sampled and analyzed by SPME-GCMS method as detailed in Example 4. A chromatographic representation of the analysis is shown in FIG. 5. Results are tabulated in Table 2.

TABLE 2

SPME-GCMS analysis of VOCs produced by the *Muscodor albus* SA-13 strain grown on barley grains.

| Entry | RT (min) | Possible Compound ID |
|---|---|---|
| 1 | 0.76 | Ethanol |
| 2 | 1.53 | Propanol |
| 3 | 2.47 | 2-Butanone, 4-hydroxy- |
| 4 | 2.53 | Ethyl Acetate |
| 5 | 3.97 | Propanoic acid, 2-methyl-, methyl ester |
| 6 | 4.45 | Propanoic acid, ethyl ester |
| 7 | 4.91 | 1-Butanol, 3-methyl- |
| 8 | 5.01 | 1-Butanol, 2-methyl- |
| 9 | 5.44 | Propanoic acid, 2-methyl-, ethyl ester |
| 10 | 5.73 | Acetic acid, 2-methylpropyl ester |
| 11 | 5.78 | Butanoic acid, 2-methyl-, methyl ester |
| 12 | 6.96 | Butanoic acid, 2-methyl-, ethyl ester |
| 13 | 7.04 | Propanoic acid, 2-methyl-, butyl ester |
| 14 | 7.39 | 1-Butanol, 3-methyl-, acetate |
| 15 | 7.42 | 1-Butanol, 2-methyl-, acetate |
| 16 | 7.91 | Propanoic acid, 2-methyl-, butyl ester |
| 17 | 8.1 | Benzene, methoxy- |
| 18 | 8.3 | Ethyl tiglate |
| 19 | 8.9 | 3-Octanone |
| 20 | 9.2 | Propanoic acid, 2-methyl-, 3-methylbutyl ester |
| 21 | 10.48 | Phenylethyl Alcohol |
| 22 | 11.96 | Acetic acid, 2-phenylethyl ester |
| 23 | 12.78 | (−)Aristolene |
| 24 | 12.95 | Cyclohexane, 1-ethenyl-1-methyl-2,4-bis(1-methylethenyl)- |
| 25 | 13.2 | Azulene, 1,2,3,4,5,6,7,8-octahydro-1,4-dimethyl-7-(1-methylethenyl)-, (1S-(1.alpha.,4.alpha.,7.alpha.)]- |
| 26 | 13.58 | Bicyclo[5.3.0]decane, 2-methylene-5-(1-methylvinyl)-8-methyl- |
| 27 | 13.66 | Azulene, 1,2,3,5,6,7,8,8a-octahydro-1,4-dimethyl-7-(1-methylethenyl)-, [1S-(1.alpha.,7.alpha.,8a.beta.)]- |
| 28 | 14.92 | Azulene, 1,2,3,5,6,7,8, 8a-octahydro-1,4-dimethyl-7-(1-methylethenyl)-, (1S-(1.alpha.,7.alpha.,8a.beta.)]- |

Identification of the VOCs produced was made via a library match with the available NIST database.

Study 3. Comparative Analysis of VOCs Produced by *Muscodor albus* CZ 620 and SA-13 Grown on Barley Grains.

Figure 6:
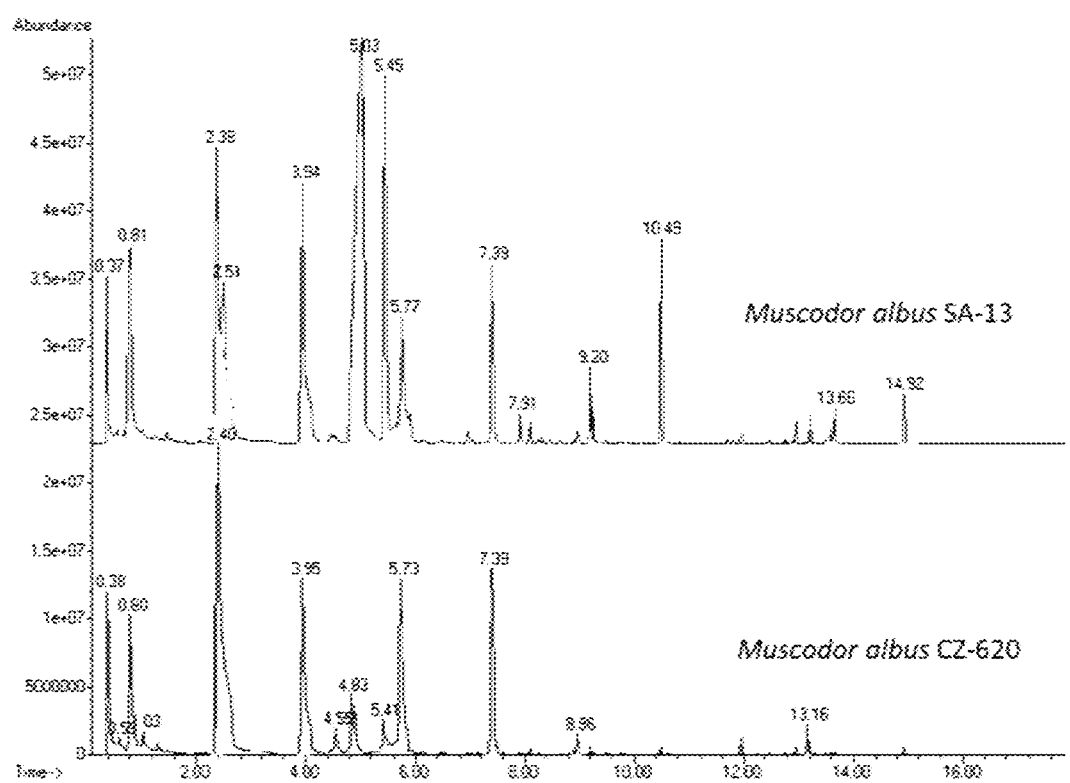
FIG. 6 shows overlayed chromatograms of VOCs produced by *Muscodor albus* CZ 620 and SA-13 as analyzed using SPME-GCMS.

Differences in the type and quantity of VOCs produced by *Muscodor albus* CZ 620 and SA-13 can be observed as shown in FIG. 6. A direct comparison of VOCs produced by the *Muscodor albus* SA-13 strain grown on barley grains is summarized in Table 3.

TABLE 3

Comparison of VOCs produced by the *Muscodor albus*
SA-13 and 620 strains grown on barley grains.

| Entry | RT (min) | Possible Compound ID | *Muscodor* Strains 620 | SA-13 |
|---|---|---|---|---|
| 1 | 0.76 | Ethanol | V | V |
| 2 | 1.53 | Propanol | V | V |
| 3 | 2.47 | 2-Butanone, 4-hydroxy- | V | V |
| 4 | 2.53 | Ethyl Acetate | V | V |
| 5 | 3.97 | Propanoic acid, 2-methyl-, methyl ester | V | V |
| 6 | 4.45 | Propanoic acid, ethyl ester | — | V |
| 7 | 4.48 | 2-Butanone, 3-hydroxy- | V | — |
| 8 | 4.58 | n-Propyl acetate | V | — |
| 9 | 4.91 | 1-Butanol, 3-methyl- | V | V |
| 10 | 5.01 | 1-Butanol, 2-methyl- | V | V |
| 11 | 5.44 | Propanoic acid, 2-methyl-, ethyl ester | V | V |
| 12 | 5.62 | Propanoic acid, 2-methyl | V | — |
| 13 | 5.73 | Acetic acid, 2-methylpropyl ester | — | V |
| 14 | 5.78 | Butanoic acid, 2-methyl-, methyl ester | V | V |
| 15 | 6.16 | Butanoic acid, ethyl ester | V | — |
| 16 | 6.96 | Butanoic acid, 2-methyl-, ethyl ester | V | V |
| 17 | 7.04 | Propanoic acid, 2-methyl-,butyl ester | — | V |
| 18 | 7.3 | 2-Butenoic acid, 2-methyl-, methyl ester (Methyl tiglate) | V | — |
| 19 | 7.39 | 1-Butanol, 3-methyl-, acetate | V | V |
| 20 | 7.42 | 1-Butanol, 2-methyl-, acetate | — | V |
| 21 | 7.91 | Propanoic acid, 2-methyl-, butyl ester | — | V |
| 22 | 8.1 | Benzene, methoxy- | — | V |
| 23 | 8.3 | Ethyl tiglate | V | V |
| 24 | 8.9 | 3-Octanone | — | V |
| 25 | 9.2 | Propanoic acid, 2-methyl-, 3-methylbutyl ester | — | V |
| 26 | 10.48 | Phenylethyl Alcohol | V | V |
| 27 | 11.96 | Acetic acid, 2-phenylethyl ester | — | V |
| 28 | 12.78 | (−)Aristolene | — | V |
| 29 | 12.95 | Cyclohexane, 1-ethenyl-1-methyl-2,4-bis(1-methylethenyl)- | — | V |
| 30 | 13.19 | 1H-3a,7-methanoazulene, 2,3,4,7,8,8a-hexahydro-3,6,8,8-tetramethyl-, [3R-(3R(3,alpha.,3a.beta.,7.beta.,8a.alpha.)]- | V | — |
| 31 | 13.2 | Azulene, 1,2,3,4,5,6,7,8-octahydro-1,4-dimethyl-7-(1-methylethenyl)-, (1S-(1.alpha.,4.alpha.,7.alpha.)]- | — | V |
| 32 | 13.58 | Bicyclo[5.3.0]decane, 2-methylene-5-(1-methylvinyl)-8-methyl- | — | V |
| 33 | 13.66 | Azulene, 1,2,3,5,6,7,8,8a-octahydro-1,4-dimethyl-7-(1-methylethenyl)-, [1S-(1.alpha.,7.alpha.,8a.beta.)]- | — | V |
| 34 | 14.92 | Azulene, 1,2,3,5,6,7,8,8a-octahydro-1,4-dimethyl-7-(1-methylethenyl)-, (1S-(1.alpha.,7.alpha.,8a.beta.)]- | V | V |

Note:
"V", compound detected; "—", compound not detected.

Study 4. GCMS Analysis of the XAD7-Trapped VOCs Produced by *M. albus* 620 and SA-13

Figure 7:
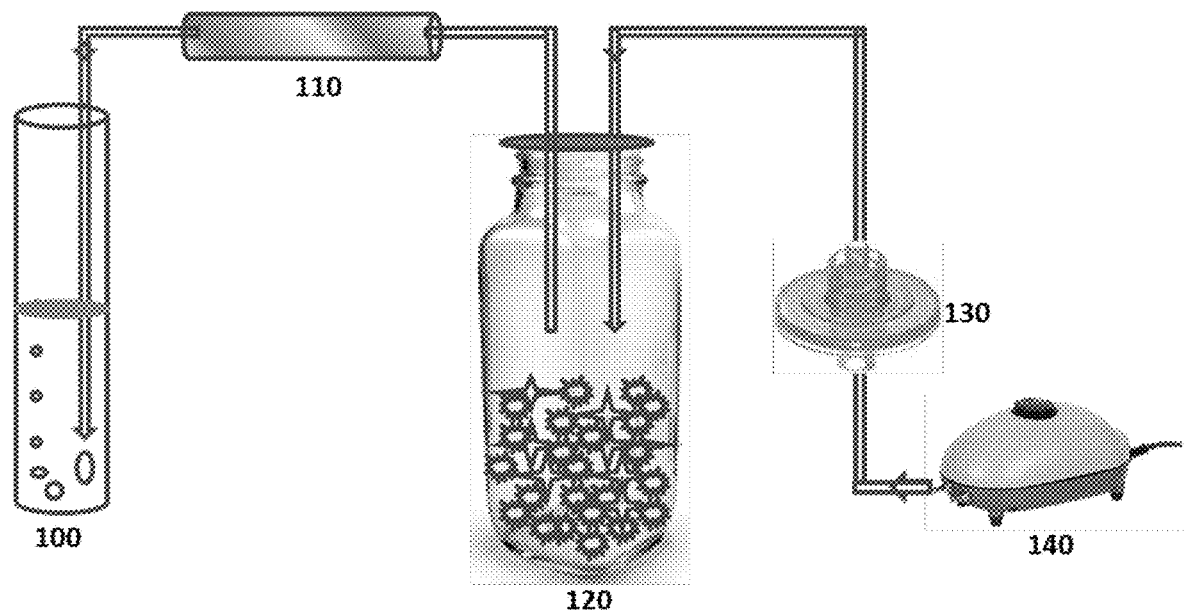
FIG. 7 is a schematic representation of the sampling process for capturing of VOCs produced by *Muscodor albus* using XAD7 resin.

An active culture of *Muscodor albus* is grown in a French Square Glass Bottle (250 mL) (120) containing autoclave-sterilized barley grains (~65 g). Filtered air (130) is passed over the culture at a steady bubbling rate via the use of an air pump (140). The exhaust gas was allowed to pass through a bed of XAD7 resin (110) and then bubbled into a test-tube (100) containing ethanol (10 mL) for 16 h as shown in FIG. 7.

Upon the completion of the sampling process, the resin was washed with MeOH (4 mL) and an aliquot (1 mL) of the washed MeOH solution was used for GCMS analysis using a Agilent 7890A gas chromatography system containing a 20 m×0.18 mm I.D. DB-VRX column with a film thickness of 1.0 μm. The column was temperature programmed as follows: 45° C. for 3 min followed to 170° C. at 15° C./min and then from 170° C. to 225° C. at 35° C. and then hold at 225° C. for 5 min. Ultra high purity helium was used as carrier gas at a rate of 55 cm/sec (1.5 mL/min) with initial column head pressure of 29 psi, inlet temperature of 150° C. and a split ratio of 60:1. The gas chromatograph was interfaced to an Agilent 5975C inert XL MSD with Triple-Axis Detector. The MS was scanned at a rate of 2.3 scans per second over a mass range of 35-360 amu. Data acquisition and processing were performed on the Agilent ChemStation software system and tentative identification of VOCs produced by *Muscodor albus* 620 and SA-13 were made by comparing the mass fragmentation pattern of the unknown with the with the available NIST database.

Figure 8:
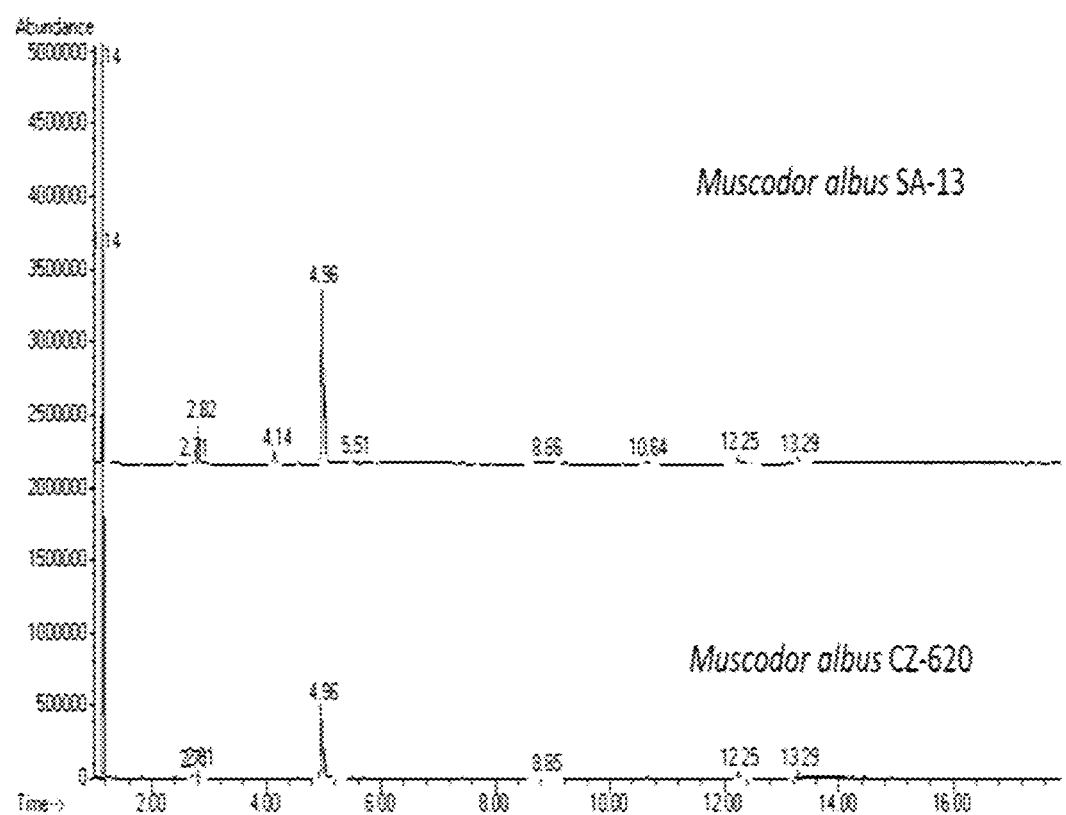
FIG. 8 shows GCMS analyses of XAD7 resin trapped VOCs produced by the *M. albus* CZ 620 and SA13 grown on barley grains.

A chromatographic representation of the VOCs produced by *Muscodor albus* CZ 620 and SA-13 and trapped in the XAD-7 resin is shown in FIG. 8. Identification of the VOCs produced was made by comparing the mass fragmentation of the unknown with the available NIST database as well as with authentic samples obtained from commercial sources. The identity of the VOCs produced is summarized in Table 4.

TABLE 4

Possible VOCs produced by *Muscodor albus* SA-13 and were trapped with XAD7 resin.

| Peak # | RT (min) | Possible Compound ID (NIST) | MW (m/z) | % of Total | Match Quality (%) | Artificial Mix (10 mL) |
|---|---|---|---|---|---|---|
| 1 | 1.14 | Ethanol | 46 | 30.6 | 86 | 3.06 |
| 2 | 2.71 | Ethyl acetate | 88 | 7.5 | 86 | 0.75 |
| 3 | 2.82 | 1-Propanol, 2-methyl- | 74 | 8.7 | 91 | 0.87 |
| 4 | 4.14 | Propanoic acid, 2-methyl-, methyl ester | 102 | 2.8 | 91 | 0.28 |
| 5 | 4.96 | 1-Butanol, 3-methyl- | 88 | 30.1 | 90 | 3.01 |
| 6 | 5.02 | 1-Butanol, 2-methyl- | 88 | 19.4 | 83 | 1.94 |
| 7 | 5.51 | Propanoic acid, 2-methyl-, ethyl ester | 116 | 0.9 | 81 | 0.09 |

*Muscodor albus* SA-13 produced all of the seven compounds trapped by XAD7, while *Muscodor albus* CZ 620 produced only five of the compounds listed (See Table 5).

TABLE 5

Comparison of XAD7 resin trapped VOCs produced by the *Muscodor albus* SA-13 and CZ 620 when grow on barley grains.

| Entry | RT (min) | Possible Compound ID | *Muscodor albus* 620 | SA-13 |
|---|---|---|---|---|
| 1 | 1.14 | Ethanol | V | V |
| 2 | 2.71 | Ethyl acetate | V | V |
| 3 | 2.82 | 1-Propanol, 2-methyl- | V | V |
| 4 | 4.14 | Propanoic acid, 2-methyl-, methyl ester | — | V |
| 5 | 4.96 | 1-Butanol, 3-methyl | V | V |
| 6 | 5.02 | 1-Butanol, 2-methyl- | V | V |
| 7 | 5.51 | Propanoic acid, 2-methyl-, ethyl ester | — | V |

Note:
"V", compound detected; "—", compound not detected.

Study 5. Effect of the Mixture of VOCs Reconstituted from the Above Mentioned Components on Pathogen Growth.

To test different combinations of the seven compounds that make up the XAD7 resin-trap volatile mixture, the 9.5-cm plates were filled with PDA, and about 3-mm$^2$ plugs of *Fusarium oxysporum* f.sp. *fragariae* and *Macrophomina phaseolina* were used as examples and were placed 1.5 cm away from the outer edges of the plates. Opposite the plug, a little less than half of the PDA was removed from the plate. Autoclaved caps from 2-ml Eppendorf tubes were used to contain the VOCs. The caps were sterilized then placed upside down on the side without the agar. The VOC mixture of 50 µl was loaded in the cap (There were two plates per fungus, and two control plates without VOCs per fungus).

All plates were double wrapped with parafilm and placed in a plastic container. The plastic container was kept in the transfer room at about 25° C. in the dark. Once growth of the pathogens in the 0.0 µl VOC controls reach the edges of the PDA plates or show adequate growth, observe/measure the growth of each fungus by measuring from the center of the plug to the furthest edge of the colony.

TABLE 6

Effect of reconstituted VOCs (artificially mixed VOCs) on the growth of *Fusarium oxysporum* and *Macrphomina phaseolina*.

| Treatments | Growth of *Fusarium* (mm)* | Growth of *Macrophomina* (mm) |
|---|---|---|
| Control without VOCs; | 19.0 A | 27.0 BC |
| Whole mix with ethanol, ethyl acetate, 2-methyl-1-Propanol, 2-methyl-/methyl ester Propanoic acid, 3-methyl-1-Butanol, 2-methyl-1-Butanol, 2-methyl-/ethyl ester Propanoic acid | 11.0 C | 19.5 CD |
| Mixture without ethanol | 12.0 BC | 16.0 D |
| Mixture without 3-methyl-1-Butanol | 13.5 ABC | 31.0 AB |
| Mixture without ethanol and ethyl acetate | 10.0 C | 20.5 CD |
| Mixture without ethyl acetate and 3-methyl-1-Butanol | 15.0 ABC | 24.0 BCD |
| Mixture without ethanol; ethyl acetate; and, 2-methyl-1-Butanol | 12.0 BC | 29.0 AB |
| Mixture without 3-methyl-1-Butanol, 2-methyl-1-Butanol, and 2-methyl-/ethyl ester Propanoic acid | 17.5 ABC | 36.0 A |

*Data with the same letter are not significantly different with Fisher Protected LSD test at p = 0.05 level.

The whole mixture containing all the VOCs showed the strongest effect on *Fusarium oxysporium* (Table 6). Other mixtures without certain components also showed efficacy and had no significant differences compared to the whole mixture. Similarly, the growth of *Macrophomina phaseolina* was similarly or greatly inhibited by the whole mixture and the mixtures without some ingredients. These results demonstrate that various components of the VOCs can be combined for controlling different disease pathogens.

Example 5

Fungicidal and Bactericidal Effect of *Muscodor albus* SA-13

Study 1. Comparison of *M. albus* SA-13 and CZ 620 on Inhibiting the Growth of Funcal Pathogens.

Split petri plates of ø10 cm with PDA were used for evaluating the inhibitive effect of the strains against plant pathogens. The following pathogens were used for the evaluation: *Botrytis cinerea*, *Fusarium oxysporum* f.sp. *fragariae*, *Pythium ultimum*, *Rhizoctonia solani*, *Sclerotinia minor*, and *Verticillium dahliae*. There were two plates for each *Muscodor* strain, and two without *Muscodor* as the blank controls for each pathogen.

A 5-mm$^2$ PDA plug of each isolate was placed 2.5 cm away from the outer edge of one side of the split petri plate. The plates were sealed and isolates were allowed to grow for 3 days at room temperature (about 25° C.). A 3-mm$^2$ PDA plug of each pathogen was placed at 1.5 cm away from the outer edge of the other side of the split plate. One *sclerotium* of *Sclerotinia minor* was placed on the agar plate instead of a plug.

The growth of each pathogen was measured from the center of the plug to the furthest edge of the colony after their water controls reached the divider in the plate. The percentage inhibition of mycelial growth is given in Table 7. The strain SA-13 showed superior inhibition on the mycelium growth of the pathogens tested. Comparatively, the strain *M. albus* CZ 620 isolated from cinnamon tree (see, for example, U.S. Pat. No. 6,911,338) was less effective on *Fusarium oxysporum* and *Pythium ultimum*.

TABLE 7

Inhibition by *Muscodor albus* strains SA-13 and CZ 620 on the mycelial growth of various plant pathogens (*Botrytis cinerea* (Bot), *Fusarium oxysporum* f. sp. *fragariae* (Fus), *Pythium ultimum* (Pyth), *Rhizoctonia solani* (Rhizo), *Sclerotinia minor* (Scler), and *Verticillium dahliae* (Vert)).

| | Inhibition (%) | | | | | |
|---|---|---|---|---|---|---|
| *Muscodor albus* | Bot | Fus | Pyth | Rhizo | Scler | Vert |
| SA-13 | 90% | 84% | 100% | 100% | 100% | 100% |
| CZ-620 | 94% | 40% | 50% | 85% | 100% | 100% |

Study 2. Selective Inhibition of *M. albus* SA-13 on Soil-borne Fungi.

Two additional plant pathogens, *Macrophomina phaseolina*, *Sclerotium rolfsii*, and one non-pathogenic fungus, *Trichoderma viride*, were used to evaluate the inhibitive effect of *M. albus* SA-13.

The above mentioned split petri plates with PDA medium were used in the test. There were two plates for the *Muscodor* strain, and two without *Muscodor* as blank control.

A 5-mm² plug of the *M. albus* SA-13 strain was placed 2.5 cm away from the outer edge of one side of the PDA plate. The *Muscodor* strain was grown for 5 days in sealed plates at room temperature (about 25° C.) and then a 3 mm² plug of each pathogen or *Trichoderma viride* was placed at 1.5 cm away from the outer edge of the other side of the split plate. The growth of each pathogen was measured as described in Study 1 and results are given in Table 8.

TABLE 8

Inhibition on the mycelial growth of fungi (*Macrophomina phaseolina* (Mac), *Sclerotium rolfsii* (Scl rol), and *Trichoderma viride* (Tricho).) by *Muscodor albus* SA-13.

| | Inhibition (%) | | |
|---|---|---|---|
| *Muscodor albus* | Mac | Scl rol | Tricho |
| SA-13 | 100% | 100% | 0% |

*Muscodor albus* strain SA-13 showed a highly inhibitive effect on all the plant pathogens. However, it did not show any inhibitative effect on the growth of the beneficial fungus *Trichoderma viride*.

Study 3. Inhibitative Effect of *M. albus* SA-13 on Bacterial Plant Pathogens.

*Muscodor albus* strain SA-13 was further evaluated for its inhibitive effect on bacterial plant pathogens with barley grains.

To culture the *Muscodor* strain, the barley grains were washed more than three times with deionized water, and soaked for 24 hours at 20° C. The water was drained off before splitting the grains evenly between autoclave bags with foam stoppers. The grains were then autoclaved for 15 minutes at 121° C. twice. Once the grains cooled, several small plugs of *Muscodor albus* strain SA-13 were added to each bag and leaving one bag non-inoculated as blank control. The fungus was grown in the bags for 11 days at room temperature. The masses of inoculated barley grains were broken up on the day of the test so the grains were less stuck together.

There were four bacteria tested: *Pectobacterium carotovorum* (Pec), *Pseudomonas syringae* (Pst), *Xanthomonas vesicatoria* (Xan), and *Clavibacter michiganensis* subsp. *michiganensis* (Clay). Each bacterium was grown on an agar medium for one day before being washed off. The $OD_{600}$ of each bacterium was adjusted to approximately 0.2 using sterile water (for all bacteria tested OD=0.2 is approximately $10^8$ cfu/ml). Using sterile water, serial dilutions were done for each bacterium up to $10^5$. From the $10^4$ and $10^5$ dilutions, 15 µl of solution was spread onto 35-mm PDA petri plates until dry. The 35-mm plates were then placed without their lids inside 10-cm petri plates next to 11 g of either the SA-13 inoculated grains, or non-inoculated sterile grains. Each plate was wrapped up with two pieces of Parafilm, placed in a sealed container and incubated at room temperature (~25° C.) in the dark.

The effect on each bacterium was determined by counting the colony forming unit (CFU) on each 35 mm plate after 1-3 days. After 3 days, the 35-mm plates were removed from the 95-mm plates, the lids were replaced, and the small plates were placed in a 25° C. incubator in the dark. After five days in the incubator the recoveries of the bacteria were determined by recounting the number of colonies on the SA-13 exposed plates. The results are given in Table 9.

TABLE 9

CFU for different concentrations of plant pathogenic bacteria after exposure to *M. albus* SA-13 grains and non-inoculated grains and CFU after 5 days of recovery from exposure to *M. albus* SA-13 grains.

| | Mean CFU/plate | | | | | |
|---|---|---|---|---|---|---|
| | Exposed to isolate SA13 | | Exposed to non-inoculated barley | | Recovery after exposure to isolate SA13 | |
| Bacterium | $10^5$ dilution | $10^4$ dilution | $10^5$ dilution | $10^4$ dilution | $10^5$ dilution | $10^4$ dilution |
| Pec | 0.0 | 0.0 | 31.0 | 358.5 | 0.0 | 0.0 |
| Pst | 0.0 | 0.0 | 7.5 | 17.5 | 0.0 | 0.0 |
| Xan | 0.0 | 0.0 | 18.5 | 185.5 | 0.0 | 0.0 |
| Clav | 0.0 | 0.0 | 56.5 | 543.5 | 22.0 | 123.5 |

*Muscodor albus* strain SA-13 completely inhibited the growth of all four pathogens and none were able to recover except *Clavibacter michiganensis* subsp. *michiganensis*, which did not show a full recovery.

Study 4. Evaluation of the Reconstituted VOCs on Inhibiting Plant Pathogens and SA-13.

Reconstituted mixes of six volatiles produced (Ethanol, Ethyl acetate, 2-methyl-1-Propanol, 2-methyl-, methyl ester Propanoic acid, 3-methyl-1-Butanol, 2-methyl-1-Butanol) by *Muscodor albus* strain SA-13 captured with the above mentioned resin trap were evaluated for their inhibitory effect on fungi.

The following fungi were used as test organisms for the VOC bioassay: *Fusarium oxysporum* f.sp. *fragariae* (Fus), *Botrytis cinerea* (Bot) and *Muscodor albus* isolate SA-13 (SA-13). A small piece of agar was removed from one side of a PDA petri plate. A 3-mm² plug of each pathogen was placed on the agar 1.5 cm away from the outer edge of the plate, opposite the empty hole. Autoclaved caps from 2-ml Eppendorf tubes were sterilized and placed upside down in the empty space. The artificial VOC mixture was placed in the upside down cap at varying volumes. The test also included control plates which contained empty caps. Each plate was wrapped up with two pieces of Parafilm, placed in a sealed container and incubated at room temperature (~25° C.) in the dark.

The % inhibition of each test organism was determined by measuring the mycelial growth from the center of the agar plug to the furthest edge of the colony. The results are given in Table 10.

TABLE 10

Inhibition of fungal pathogens after exposure to an *M. blbus* SA-13 artificial VOC mix with six compounds at different volumes.

| Pathogen | Inhibition (%) | | | | |
|---|---|---|---|---|---|
|  | 5 ul | 20 ul | 35 ul | 50 ul | 75 ul |
| Fus | −8.6 | 5.2 | 13.8 | 25.9 | 43.1 |
| Bot | −11.9 | 6.0 | 31.3 | 49.3 | 76.1 |
| SA-13 | 4.7 | 11.6 | 20.9 | 27.9 | 44.2 |

The 6 compound mixture at 35 µl was able to significantly inhibit the growth of all fungi tested. There is also a positive relationship between the dose and the mycelial inhibition.

Study 5. Reepeated Evaluation of the Reconstituted VOCs on Inhibiting Plant Pathogens The reconstituted mixture of the seven volatiles produced (Ethanol, Ethyl acetate, 2-methyl-1-Propanol, 2-methyl-, methyl ester Propanoic acid, 3-methyl-1-Butanol, 2-methyl-1-Butanol, 2-methyl-, ethyl ester-Propanoic acid) by *Muscodor albus* strain SA-13 captured with the above mentioned resin trap were evaluated for their inhibitive effect on plant pathogens.

The following plant pathogens were used as test organisms for the VOC bioassay: *Verticillium dahliae* (Vert), *Macrophomina phaseolina* (Mac), *Rhizoctonia solani* (Rhizo), *Pythium ultimum* (Pyth), *Fusarium oxysporum* f.sp. *fragariae* (Fus), and *Sclerotium rolfsii* (Scl rol). Slightly less than half of the agar was removed from one side of a PDA petri plate. A 3-mm$^2$ plug of each pathogen was placed on the agar 1.5 cm away from the outer edge of the plate, opposite the empty side. Autoclaved caps from 2-ml Eppendorf tubes were sterilized and placed upside down on the empty side of the plate. The artificial VOC mixture was placed in the upside down cap at varying volumes. The test also included control plates which contained empty caps. Each plate was wrapped up with two pieces of Parafilm, placed in a sealed container and incubated at room temperature (~25° C.) in the dark.

The percentage inhibition of each test organism was determined by measuring the mycelial growth from the center of the agar plug to the furthest edge of the colony. The test was repeated with a higher dose of the VOC mixture for all fungi that were not significantly inhibited in the initial test. The results are given in Table 11.

TABLE 11

Inhibition of soil-borne pathogens after exposure to an SA-13 artificial VOC mix at different volumes.

| | Inhibition (%) | |
|---|---|---|
| Pathogen | 35 μl | 75 μl |
| Vert | 9.5 | 62.5 |
| Mac | 7.1 | 53.5 |
| Rhizo | 53.6 | — |
| Pyth | 34.7 | — |
| Fus | 24.1 | — |
| Scl rol | 65.8 | — |

"—": *Rhizoctoniasolani*, *Pythium ultimum*, *Fusarium oxysporum* f. sp. *fragariae*, and *Sclerotium rolfsii* pathogens were not tested at the 75 microliter volume, since their growth was inhibited by lower volume of VOCs.

The artificial volatile mixture at was able to inhibit the growth of *Fusarium oxysporum* f.sp. *fragariae, Pythium ultimum, Rhizoctonia solani*, and *Sclerotium rolfsii*. At 75 μl, the mixture was able to inhibit the growth of *Macrophomina phaseolina* and *Verticillium dahliae*.

Study 6. Repeated Evaluation on the Inhibition of Soilborne Pathogens by *M. albus* SA-13.

*Muscodor albus* strain SA-13 at different doses was further evaluated for its inhibitive effect on plant pathogens.

To culture the *Muscodor* strain, the barley grains were washed three times with tap water, and soaked for 24 hours at 20° C. The water was rewashed and drained off before splitting the grains evenly between autoclave bags with foam stoppers. The grains were then autoclaved for 15 minutes at 121° C. two times. Once the grains cooled, each bag was inoculated with 12 ml of a 10-day culture of *Muscodor albus* strain SA-13 grown on potato dextrose broth. The fungus was grown in the bags for 9 days at 25° C. The masses of inoculated barley grains were then broken up and allowed to air-dry until seed moisture was <10%.

The dried grains were ground with a coffee grinder and particles that went through a 2-mm sieve and were saved by a 45 μm sieve were saved for testing. The grains were rehydrated with water and different doses of the grains were placed in a single center well of a 6-well plate to grow for three days. The three wells adjacent to the grain-occupied well contained PDA. The two non-adjacent wells remained empty for the duration of the test.

The following plant pathogens were used as test organisms for the dose bioassay: *Fusarium oxysporum* f.sp. *fragariae* (Fus), *Rhizoctonia solani* (Rhizo), and *Pythium ultimum* (Pyth). A 3-mm$^2$ plug of each pathogen was placed on the agar in the center of the PDA filled well, each plate holding one dose of the grain and one plug of each pathogen. The test also included control plates that contained no barley grain. Each plate was sealed with tape, and incubated until the controls reached the edges of the wells, or showed adequate growth.

The percentage inhibition of each plant pathogen was determined by measuring the mycelial growth from the center of the agar plug to the furthest edge of the colony. The results are given in Table 12.

TABLE 12

Inhibition of *Muscodor albus* strain SA-13 at different doses on the mycelial growth of plant pathogens.

| | Inhibition (%) | | |
|---|---|---|---|
| *M. albus* (g) | Fus | Rhizo | Pyth |
| 0.05 | −12.5 | 66.7 | 100.0 |
| 0.1 | −12.5 | 100.0 | 100.0 |
| 0.5 | 12.5 | 66.7 | 100.0 |
| 1.0 | 75.0 | 100.0 | 100.0 |
| 2.0 | 75.0 | 100.0 | 100.0 |
| 3.0 | 75.0 | 100.0 | 100.0 |
| 5.0 | 62.5 | 100.0 | 100.0 |

*Muscodor albus* strain SA-13 showed inhibition of the mycelial growth of all the pathogens tested.

Study 7. Inhibition of More Soilborne Pathogens by *M. albus* SA-13.

A repeated test on *Muscodor albus* strain SA-13 at different doses was conducted to evaluate its inhibitive effect on additional plant pathogens.

The grains used in Study 6 were also used in this study. The following plant pathogens were used as test organisms for the bioassay: *Verticillium dahliae* (Vert), *Macrophomina phaseolina* (Mac), and *Sclerotium rolfsii* (Scl rol). The barley grain culture and plant pathogens were arranged in the plates as described in Study 6.

The percentage inhibition of each test organism was determined by measuring the mycelial growth from the center of the agar plug to the furthest edge of the colony. The results are given in Table 13.

TABLE 13

Inhibition of *Muscodor albus* strain SA-13 at different doses on the mycelial growth of plant pathogens.

| M. albus (g) | Inhibition (%) | | |
|---|---|---|---|
| | Vert | Mac | Scl rol |
| 0.05 | 100.0 | 100.0 | 100.0 |
| 0.1 | 100.0 | 100.0 | 100.0 |
| 0.5 | 100.0 | 100.0 | 100.0 |
| 1.0 | 100.0 | 100.0 | 100.0 |
| 3.0 | 100.0 | 100.0 | 100.0 |

*Muscodor albus* strain SA-13 showed complete inhibition of the mycelial growth of all pathogens at all doses tested.

Study 8. Control of Soilborne Diseases by Incorporation of *M. albus* SA-13 in Soil.

*Muscodor albus* isolate SA-13 was further evaluated for its efficacy in controlling *Rhizoctonia solani* on soybean.

To culture the *Muscodor* strain, the barley grains were washed with deionized water, and soaked for 24 hours. The water was drained off before splitting the grains evenly between autoclave bags with foam stoppers. The grains were then autoclaved for 15 minutes at 121° C. twice. Once the grains cooled, several small plugs of *Muscodor albus* strain SA-13 were added to each bag. The pathogen was grown in the bags for 12 days at room temperature. The masses of inoculated barley grains were broken up on the day of the test so the grains were less stuck together.

*Rhizoctonia* inoculum was mixed into artificial soil media at a rate of 1:1200. The inoculated media was placed into plastic boxes at 1 L per box. SA-13 barley seeds were then mixed into the infested soil media at the rates 2 mg/ml, 4 mg/ml, and 6 mg/ml. In separate treatments, SA-13 seeds were scattered over the top of the inoculated soil media at 2.8 mg/cm$^2$, 28 mg/cm$^2$, and 56 mg/cm$^2$. The boxes were watered, closed, and sealed with tape for two days. After two days of treatment, 24 soybean seeds were planted in each box before re-sealing the boxes and placing them under fluorescent lights for ten days.

The soybean emergence after ten days was determined by counting the number of emerged seedlings within each box. The results are given in Table 14.

TABLE 14

Emergence of soybeans planted in *Rhizoctonia solani* infested soil treated with SA-13 grains either incorporated into the soil or surface treated.

| Treatment | Emergence (%) |
|---|---|
| Non-treated | 0.0 |
| 2.0 mg/ml soil incorporation | 1.4 |
| 4.0 mg/ml soil incorporation | 9.7 |
| 6.0 mg/ml soil incorporation | 4.2 |
| 2.8 mg/cm$^2$ surface treatment | 0.0 |
| 28.0 mg/cm$^2$ surface treatment | 33.3 |
| 56.0 mg/cm$^2$ surface treatment | 31.3 |

When incorporated into the soil or surface apllied, *M. albus* SA-13 grown on barley grains increased emergence of soybean seeds.

Study 9. Use of *M. albus* SA-13 for Controlling Strawberry Postharvest Diseases.

*Muscodor albus* strain SA-13 was further evaluated for its use in controlling post-harvest disease caused by *Botrytis cinerea*.

To culture the *Muscodor* strain, barley grains were washed three times with tap water, and soaked for 24 hours at 20° C. The grains were rewashed and the water was drained off before splitting the grains evenly between autoclave bags with foam stoppers. The grains were then autoclaved for 15 minutes at 121° C. two times. Once the grains cooled, each bag was inoculated with 10 ml of a 7-day culture of *Muscodor albus* strain SA-13 grown in potato dextrose broth. The fungus was grown in the bags for 11 days at 25° C. The masses of inoculated barley grains were then broken up and allowed to air-dry until seed moisture was <10%. The grains were rehydrated with water at 80% of their mass and allowed to grow in a humid environment for four days prior to use.

The *B. cinerea* inoculum was prepared by flooding a mature culture in an agar plate with sterile water, filtering out any mycelia, and adjusting the concentration to approximately 10$^5$ conidia/ml. Organic strawberries were washed with tap water, surface sterilized, and rinsed three times with sterile water. After allowing the fruit surface to dry, each fruit was dipped in the inoculum for 5 seconds and placed on a rack in a crisper box. After all fruits were inoculated, the rehydrated *M. albus* SA-13 barley grains were placed inside the crisper boxes, which were then flooded with a small amount of water, sealed with tape, and placed in darkness at ~25° C. for 6 days. There were three different doses of *M. albus* SA-13 grown barley grains and a control box that did not contain any *M. albus* SA-13.

The severity of the disease was determined by estimating the precentage coverage of the pathogen growth on each strawberry fruit. The results are given in Table 15.

TABLE 15

Mycelia and rot coverage on strawberries inoculated with *Botrytis* and treated with SA-13 grains.

| M. albus (g) | Mycelia (%) | Rot (%) |
|---|---|---|
| 0.0 | 65.0 A* | 75.5 A |
| 1.0 | 0.0 B | 46.5 B |
| 5.0 | 0.0 B | 9.0 C |
| 10.0 | 0.0 B | 15.0 C |

*Data with the same letter are not significantly difference according to Fisher Protected LSD at p = 0.05 level.

When contained in a sealed box, *M. albus* SA-13 grown on barley grains completely inhibited the development of *Botrytis* mycelia growth and reduced the development of rot on strawberries.

Study 10. Use of *M. albus* SA-13 for Controlling Citrus Fruit Postharvest Diseases

*Muscodor albus* strain SA-13 was further evaluated for its inhibitive effect on postharvest pathogen *Penicillium digitatum* with barley grain medium.

The grains and method of rehydrating the grains used in Study 9 were also used in this study.

The *Penicillium* inoculum was prepared by flooding a mature culture in an agar plate with sterile water, filtering out any mycelia, and adjusting the concentration to approximately 10$^6$ conidia/ml. Using a 5-mm diameter borer, skin deep lesions were made on organic navel oranges. The oranges were then washed with tap water, surface sterilized, and rinsed three more times with sterile water. After allowing the fruit surface to dry, each lesion was inoculated with 15 μl of inoculum. The fruit were stored in crisper boxes with grains as described in Study 9.

The severity of the disease was determined by measuring the widest diameter of the rotting region on the surface of each orange. The results are given in Table 16.

TABLE 16

Control of fruit rot of citrus caused by the *Penicillium* sp..

| M. albus (g) | Lesion (0 mm)* |
|---|---|
| 0.0 | 16.8 A |
| 1.0 | 8.4 B |
| 5.0 | 10.6 B |
| 10.0 | 5.6 B |

*Data with the same letter are not significantly different from each other according to Fisher's Protected LSD at p = 0.05 level.

When contained in a sealed box, the barley grains grown with *M. albus* SA-13 reduced the development of *Penicillium* rot on citrus.

Example 6

Nematicidal Effects of *Muscodor albus* Strains SA-13 and CZ 620

Study 1. Evaluation of Nematicidal Activity of *Muscodor albus* SA-13 on PDA.

The 10-cm split petri dishes with PDA were used for evaluating the mortality effect of the strains on plant parasitic nematodes *Meloidogyne* spp. The nematodes used in the tests were a mixed culture of *M. incognita* and *M. hapla* maintained on tomato roots in the growth room. There was one plate for each *Muscodor* strain, and one without *Muscodor* as the blank control for the nematodes.

A 5-mm² PDA plug of each isolate was placed 2.5 cm away from the outer edge of one side of the split petri dish plate. The plates were sealed and isolates were allowed to grow for four days at room temperature (about 25° C.). An aliquot of 62 μl second stage juveniles (J2s) suspension, obtained by adding water into newly hatched *Meloidogyne* spp. J2 from eggs and containing about 14-15 J2s per aliquot, was placed at 1.5 cm away from the outer edge of the other side of the split plate. The plates were sealed with parafilm and put in a sealed container. The plates were incubated in darkness at room temperatures before taking any data.

The mortality of the J2s was recorded under a dissecting microscope at 24, 48, 72 and 144 hours after incubation. In general, there was a trend with increasing percentage of mortality (10 to 100%) of nematode J2s after 24 hours of co-incubation with *Muscodor* strains. The percentage of mortality of nematode J2s with time is shown in Table 17.

TABLE 17

Mortality effects of *Muscodor albus* strain SA-13 on plant parasitic nematodes of *Meloidogyne* spp.

| Muscodor albus | 24 hours | 48 hours | 72 hours |
|---|---|---|---|
| SA-13 | 10% | 90% | 95% |

*Muscodor albus* SA-13 showed mortality effects on the tested *Meloidogyne* spp. nematodes.

Study 2. A Repeated Evaluation of Nematicidal Activity of *M. albus* SA-13.

A repeated test of Study 1 was conducted with two plates of each *Muscodor* strain, two without *Muscodor* as blank controls and two with 1% Avid commercial nematicide as positive controls. The 10-cm split petri dishes with PDA were used for evaluating the mortality effect of the strains on plant parasitic nematodes of *Meloidogyne incognita*. The nematode was cultured on tomato root with a southern California origin.

A 5-mm² PDA plug of each isolate was placed 2.5 cm away from the outer edge of one side of the split petri dish plate. The plates were sealed and isolates was allowed to grow for four days at room temperature (about 25° C.). An aliquot of 80 μl second stage juveniles (J2s) of *M. incognita* suspension, obtained by adding water into newly hatched of J2s from eggs and comprised of around 5-20 J2s, was placed at 1.5 cm away from the outer edge of the other side of the split plate. A mixture of an 80 μl aliquot of J2 suspension with the same amount of 2% Avid served as positive control in a split plate without any grains. The plates were sealed with parafilm. All plates with the same *Muscodor* strains were put in a plastic bag and zipped to avoid the potential mixing effects of volatiles released from different strains. Plates in individual bags were put in a sealed container and incubated in darkness at room temperatures before taking any data.

The total number of nematode J2s in each aliquot of the nematode suspension, and the number of the nematodes J2s that showed mortality in each aliquot, was recorded under a dissecting microscopes at 24, 48, 72 and 144 hours after incubation. The percentage of J2 mortality was then calculated. In general, there was a trend with an increasing percentage of mortality (0 to 87%) of nematode J2s after 24 hours of co-incubation with *Muscodor* strains. The strain SA-13 showed superior mortality effect on the *M. incognita* J2s when compared with the original strain *M. albus* CZ-620 isolated from cinnamon tree. The effects of *Muscodor albus* strains SA-13 and CZ 620 on nematode J2s mortality are shown in Table 18.

TABLE 18

Mortality effects of *Muscodor albus* strain SA-13 and CZ 620 on plant parasitic nematodes of *Meloidogyne incognita*.

| Muscodor albus | 24 hours | 48 hours | 72 hours |
|---|---|---|---|
| SA-13 | 20% | 85% | 74% |
| CZ 620 | 0% | 0% | 14% |

Study 3: Evaluation of Nematicidal Activity of *Muscodor albus* SA-13 on Barley Grains.

The nematodes used in the test were a mixed culture of *M. incognita* and *M. hapla* maintained on tomato roots. There was one plate for each *Muscodor* strain, and one without *Muscodor* strains as a blank control. To culture the *Muscodor* strains, the barley grains were washed more than three times with deionized water, and soaked for 24 hours at 20° C. The water was drained off before splitting the grains evenly between autoclave bags with foam stoppers. The grains were then autoclaved for 15 minutes at 121° C. twice. Once the grains cooled, several small plugs of each *Muscodor albus* strain were added to each bag and leaving one bag non-inoculated as blank control. The foam stoppers were replaced with autoclaved rubber stoppers after putting the *Muscodor* plugs in. The *Muscodor* strains were grown in the bags for 13 days at room temperature. The masses of inoculated barley grains were periodically broken up so the grains were less stuck together.

Half of each split plate was filled with nematode J2 suspension and the other half was filled with 20 ml barley grains grown with *Muscodor* strains or with non-inoculated grains as blank controls. An aliquot of 62 µl J2 suspension, obtained by adding water into newly hatched *Meloidogyne* spp. J2 from eggs and containing around 14-15 J2s per aliquot, was placed at 1.5 cm away from the outer edge of the other side of the split plate. The plates were sealed with parafilm and put in a sealed container. The plates were incubated in darkness at room temperatures before taking any data.

The mortality of the J2s was recorded under a dissecting microscope at 24, 48, 72 and 144 hours after incubation. In general, there was a trend with increasing percentage of mortality (0 to 100%) of nematode J2s after 24 hours of co-incubation with *Muscodor* strains. The strain SA-13 showed superior mortality effect on the nematode J2s. Comparatively, the strain *M. albus* CZ 620 was less effective on killing the nematode J2s even after 144 hours. The percentage of mortality of nematode J2s as a function of time is shown in Table 19.

TABLE 19

Mortality effects of *Muscodor albus* strain SA-13 and CZ 620 on plant parasitic nematodes of *Meloidogyne* spp.

| *Muscodor albus* | 24 hours | 48 hours | 72 hours |
|---|---|---|---|
| SA-13 | 70% | 95% | 95% |
| CZ 620 | 0% | 0% | 0% |

Study 4: A Repeated Evaluation of Nematicidal Activity of *M. albus* SA-13 on Barley Grains.

A repeated test described in Study 3 was conducted with two plates of each of *Muscodor* strain, two without *Muscodor* as blank controls and two with 1% Avid as positive controls. *Muscodor albus* strains were further evaluated for their mortality effect on plant parasitic nematodes of *Meloidogyne incognita* with barley grain medium.

To culture the *Muscodor* strains, the barley grains were washed more than three times with deionized water, and soaked for 24 hours at 20° C. The water was drained off before splitting the grains evenly between autoclave bags with foam stoppers. The grains were then autoclaved for 15 minutes at 121° C. twice. Once the grains cooled, several small plugs of each *Muscodor albus* strain were added to each bag and leaving one bag non-inoculated as blank control. The foam stoppers were replaced with autoclaved rubber stoppers after putting the *Muscodor* plugs in. The *Muscodor* strains were grown in the bags for 13 days at room temperature. The masses of inoculated barley grains were periodically broken up so the grains were less stuck together.

Half of each split plate was filled with nematode J2 suspension and the other half was filled with 20 ml barley grains grown with *Muscodor* strains or with non-inoculated grains as blank controls. A mixture of 80 µl aliquot of J2 suspension with the same amount of 2% Avid served as positive control in a split plate without any grains.

An aliquot of 80 µl J2s suspension, obtained by adding water into newly hatched *M. incognita* J2 from eggs and comprised of around 14-15 J2s per aliquot, was placed at 1.5 cm away from the outer edge of the other side of the split plate. All plates were sealed with parafilm. The plates with the same *Muscodor* strains were put in one plastic bag and zipped to avoid the potential mixing effects of volatiles released from different strains. The plates were sealed with Parafilm and put in a sealed container. The plates were incubated in darkness at room temperatures before taking any data.

The total number of nematode J2s in each aliquot of the nematode suspension, and the number of the nematodes J2s showing mortality was recorded at 24, 48, 72 and 144 hours after incubation under a dissecting microscope. The percentage of J2 mortality was calculated. In a general trend, nematode J2s showed increasing percentage of mortality (27 to 92%) after 24 hours of co-incubation with *Muscodor* strains. The strain SA-13 showed superior mortality effect on the *M. incognita* J2s when compared with the original strain *M. albus* 620 isolated from cinnamon tree. The percentage of mortality of nematode J2s as a function of time is shown in Table 20.

TABLE 20

Mortality effects of *Muscodor albus* strain SA-13 and CZ 620 on plant parasitic nematodes of *Meloidogyne incognita*

| *Muscodor albus* | 24 hours | 48 hours | 72 hours |
|---|---|---|---|
| SA-13 | 27% | 33% | 75% |
| CZ 620 | 29% | 44% | 67% |

Study 5: Nematicidal Activity of the Artificial Mix of Seven VOCs from *M. albus* SA-13.

The seven volatile organic compounds (VOCs) that were trapped using XAD7 resin were reconstituted. Samples were prepared by artificially mixing the seven compounds. The eggs of root-knot nematodes (*Meloidogyne incognita*) were extracted from tomato plants that were inoculated and incubated in the greenhouse for about two months. The eggs extracted were set to hatch into second stage juveniles (J2s) on two layers of Kimwipe paper supported by wire mesh on a plastic beaker. The suspension of J2s were collected and diluted to 300 J2s/100 µl of deionized water.

Filter paper was cut to fit the petri dish (95 mm×15 mm) and moistened with deionized water. A single well concavity slide and a cap of 2 ml centrifuge tube were placed in the petri dish. 100 µl of the J2s suspension was pipetted onto the well of concavity slide. 0 µl, 25 µl, 75 µl, 100 µl, and 125 µl of samples were pipetted onto the centrifuge tube cap. A 75 µl of deionized water was used as a negative control. Four caps of 15 ml centrifuge tubes (about 11 $cm^3$) in one petri dish were used for holding barley grains that were colonized by *M. albus* SA-13 as a positive control. Each treatment had two replicates.

The petri dishes were capped and sealed with two layers of Parafilm. All petri dishes were placed in a plastic box. The box was sealed with marking tape, covered with aluminum foil, and incubated at around 26.7° C. for 48 hours.

After 48-hour incubation, the nematode drops on concavity slides were observed under a stereoscope. The percentage of immobilized J2s was visually scored on a scale of 0 to 100% (Table 21). Curled or moving J2s were considered mobile; straight J2s were considered immobile.

TABLE 21

Immobility of *Meloidogyne incognita* J2s in concavity slide 48 hours after exposure to the artificial mix of VOCs from *M. albus* SA-13.

| Treatment | Immobility (%)* |
|---|---|
| 0.0 μl VOC sample | 0.0 ± 0.0 c |
| 25.0 μl VOC sample | 75.0 ± 7.1 a |
| 75.0 μl VOC sample | 82.5 ± 3.5 a |
| 100.0 μl VOC sample | 82.5 ± 3.5 a |
| 125.0 μl VOC sample | 85.0 a |
| 75.0 μl deionized water | 0.0 ± 0.0 c |
| 11.0 cm$^3$ *M. albus* SA-13 grown barley grains | 22.5 ± 3.5 b |

*Data are means ± standard deviations (SD) with two replicates. Data without SD were data from one replicate because solution in one of the replicates evaporated and nematodes died prematurely. The values followed by a different letter in the same column indicate significant difference between treatments at p = 0.05 according to Fisher's LSD test.

After the percentage of immobilized J2s in concavity slide was scored, 20 μl drops from the concavity slide were pipetted onto the surface of 1.2% water agar in 6-well plates. After the drop dried in a fume hood, a circle was drawn around the boundary of the 20 μl drop of the J2s at the bottom of the 6-well plate. The number of J2s in the circle was counted and recorded as the total J2s. The plates were left at room temperature (about 25° C.) for 24 hours. Then the number of J2s still remaining in the circle was counted and recorded as the immobile J2s. The percentage of immobilized J2s was calculated as immobile J2s/total J2s×100 (Table 22). For treatments with 25 μl, 75 μl, and 125 μl of synthetic compounds, only 0-2 J2s were transferred on the agar. Any transferred J2s of those samples did not move out of the circle.

TABLE 22

Immobility of *Meloidogyne incognita* J2s on 6-well plate 24 hours after exposure to the artificial mix of seven VOCs from *Muscodor albus* SA-13.

| Treatment | Immobility (%)* |
|---|---|
| 0.0 μl VOC sample | 23.6 ± 2.0 c |
| 25.0 μl VOC sample | 100.0 ± 0.0 a |
| 75.0 μl VOC sample | 100.0 ab |
| 100.0 μl VOC sample | 100.0 ab |
| 125.0 μl VOC sample | — |
| 75.0 μl deionized water | 23.0 ± 6.9 c |
| 11.0 cm$^3$ *M. albus* SA-13 grown barley grains | 66.3 ± 23.1 b |

*Data are means ± standard deviations (SD) with two replicates. Data without SD are data from one replicate because one of the replicates had no nematodes successfully transferred onto the 6-well plate. The values followed by a different letter in the same column indicate significant difference between treatments at p = 0.05 level according to Fisher's LSD test.
"—": No nematodes were successfully transferred to evaluate the immobility.

*M. incognita* J2s became straight, characteristic to dead nematodes, in the presence of the reconstituted VOCs for 48 hours. They failed to recover in the absence of the VOC mixture after 24 hours.

Study 6: Nematicidal Activity of *Muscodor albus* SA-13 Grown Barley Grains.

Eggs and J2 of root-knot nematodes *M. incognita* were extracted and prepared in the same way as described previously in Study 5. Dry ground barley inoculated with *M. albus* SA13 was rehydrated with water at 80% (w:w) for 24 hours at room temperature before test. Filter paper was cut to fit undivided petri dish (95 mm-15 mm) or divided petri dish of the same size. The filter paper was moistened with deionized water. A single well concavity slide holding 100 μl of J2 suspension and a 35-mm petri dish holding 0.05 g, 0.1 g, and 0.5 g of wet ground barley with *M. albus* SA-13 were placed in the 95 mm×15 mm undivided petri dish. A blank 35-mm petri dish without ground barley was set for the negative control. For 1 g and 2 g of wet ground barley grains, divided petri dishes without 35-mm petri dish were used to correlate increasing surface area of ground barley with increasing mass. Each treatment had two replicates. All petri dishes were sealed with two layers of Parafilm and placed in a plastic box. The box was sealed with marking tape, covered with aluminum foil, and incubated at about 26° C. for 48 hours.

After 48-hour incubation, the nematode drops on the concavity slide were observed under a stereoscope. The percentage of immobilized J2s was visually scored based on a scale of 0 to 100% (Table 23). Curled or moving J2s were considered mobile; straight J2s were considered immobile. One replicate of 0.05 g ground barley did not show any nematicidal activity because the surface of the ground barley showed no indication of growth of *M. albus* SA-13.

TABLE 23

Immobility of *Meloidogyne incognita* J2s on concavity slide 48 hours after exposure to the ground barley grains with *Muscodor albus* SA-13.

| Treatment | Immobility (%)* |
|---|---|
| Check, barley grains | 0.0 ± 0.0 c |
| 0.05 g *M. albus* SA-13 barley grains | 27.5 ± 31.8 bc |
| 0.1 g *M. albus* SA-13 barley grains | 72.5 ± 3.5 bc |
| 0.5 g *M. albus* SA-13 barley grains | 60.0 ± 14.1 ab |
| 1.0 g *M. albus* SA-13 barley grains | 80.0 ± 7.1 a |
| 2.0 g *M. albus* SA-13 barley grains | 90.0 ± 0.0 a |

*Data are means ± standard deviations (SD) with two replicates. The values followed by a different letter in the same column indicate significant difference between treatments at p = 0.05 level according to Fisher's LSD test.

After the percentage of immobilized J2s in petri dish was scored, 20 μl drops from the concavity slide were pipetted onto the surface of 1.2% water agar in 6-well plates. After the drop dried in a fume hood, a circle was drawn around the boundary of the 20 μl drop of the J2s at the bottom of the 6-well plate. The number of J2s in the circle was counted and recorded as the total J2s. The plates were left at room temperature (about 25° C.) for 24 hours. Then the number of J2s still remaining in the circle was counted and recorded as the immobile J2s. The percentage of immobilized J2 was calculated as immobile J2s/total J2s×100 (Table 24).

TABLE 24

Immobility of *Meloidogyne incognita* J2s on 6-well plate with 24-hour exposure to the ground barley grains with *Muscodor albus* SA-13

| Treatment | Immobility (%)* |
|---|---|
| Check, barley grains | 20.6 ± 1.7 c |
| 0.05 g *M. albus* SA-13 barley grains | 41.0 ± 34.1 bc |
| 0.1 g *M. albus* SA-13 barley grains | 73.1 ± 19.5 ab |
| 0.5 g *M. albus* SA-13 barley grains | 77.6 ± 2.5 ab |
| 1.0 g *M. albus* SA-13 barley grains | 80.9 ± 2.5 ab |
| 2.0 g *M. albus* SA-13 barley grains | 90.7 ± 10.9 a |

*Data are means ± standard deviations (SD) with two replicates. The values followed by a different letter in the same column indicate significant difference between treatments at p = 0.05 level according to Fisher's LSD test.

In summary, *M. incognita* J2s became straight, characteristic to dead nematodes, in the presence of *M. albus* SA-13 on rehydrated ground barley grains. Most J2s failed to move out of the circle in the absence of the barley after 24 hours though the bodies of J2 were curved.

Example 7

Insecticidal Effect of *Muscodor albus* SA-13

Study 1. Effect of *M. albus* SA-13 on Armyworm Eggs.

Two small petri dishes containing approximately 20 g of autoclaved barley grains grown with *M. albus* were placed in a plastic box (approximately 2800 cm$^3$ in volume). A companion box was set up at room temperature without the petri dishes of fungus. Then 48-well microtitre plates containing beet armyworm (*Spodoptera exigua*) eggs that had been overlaid onto artificial diet were introduced into each box. After three days, the eggs in the box without the *M. albus* SA-13 began to hatch for 48.0%. The armyworm eggs did not hatch (0.0%) in the box containing the barley culture of *M. albus* SA-13.

Study 2. Re-Evaluation of *M. albus* SA-13 on Armyworm Eggs.

Petri dishes containing different amounts (1 g, 5 g, and 10 g) of *M. albus* SA-13 grown barley grains were placed in plastic boxes (approximately 2800 cm$^3$ in volume). A separate box was set up at room temperature without the petri dishes of the fungus. Then 48-well microtitre plates containing beet armyworm (*Spodoptera exigua*) eggs that had been overlaid onto artificial diet were introduced into each box. After three days, the eggs in the box without the *M. albus* SA-13 began to hatch. After 6 days, each of the 48-well microtitre plates were evaluated for hatching rates.

The number of hatched larvae exposed to 0, 1, 5, and 10 g of *M. albus* SA-13 barley grains were 82.0, 96.0, 38.0 and 0.0, respectively. The *M. albus* SA-13 inhibited the hatching of armyworm eggs.

Deposit of Biological Material

The following biological material has been deposited under the terms of the Budapest Treaty with the Agricultural Research Culture Collection (NRRL), 1815 N. University Street, Peoria, Ill. 61604 USA, and given the following number:

| Deposit | Accession Number | Deposit Date |
| --- | --- | --- |
| *Muscodor albus* Strain SA-13 | NRRL B-50774 | Aug. 31, 2012 |

The strain has been deposited under conditions that assure that access to the culture will be available during the pendency of this patent application to one determined by the Commissioner of Patents and Trademarks to be entitled thereto under 37 C.F.R. § 1.14 and 35 U.S.C. § 122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by government action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method for modulating pest infestation and/or phytopathogenic infection in a plant comprising the step of:
    applying to the plant and/or seeds and/or substrate used for growing said plant an effective amount of a pesticidal composition comprising *Muscodor albus* strain SA-13 (NRRL Accession No. B-50774) fermentation, wherein said strain produces volatile compounds comprising 3-octanone, (−) aristolene, acetic acid 2-methylpropyl ester, propanoic acid 2-methyl-methyl ester, and propanoic acid 2-methyl-butyl ester;
    wherein said pest comprises *Meloidogyne* spp., and wherein said phytopathogenic infection comprises *Fusarium* spp., *Pythium* spp. and/or *Rhizoctonia* spp.

2. The method according to claim 1, wherein said pesticidal composition further comprises a fungicide, bactericide, nematicide and/or insecticide.

3. The method according to claim 1, wherein said pesticidal composition further comprises a carrier, diluent, surfactant or adjuvant.

4. A method for modulating pest infestation and/or phytopathogenic infection in a plant comprising the steps of:
    (a) applying to the plant and/or seeds and/or substrate used for growing said plant an effective amount of a pesticidal composition comprising *Muscodor albus* strain SA-13 (NRRL Accession No. B-50774) fermentation, wherein said strain produces volatile compounds comprising 3-octanone, (−) aristolene, acetic acid 2-methylpropyl ester, propanoic acid 2-methyl-methyl ester, and propanoic acid 2-methyl-butyl ester; and
    (b) growing said plant and/or seeds;
    wherein said pest comprises *Meloidogyne* spp., and wherein said phytopathogenic infection comprises *Fusarium* spp., *Pythium* spp. and/or *Rhizoctonia* spp.

5. The method according to claim 4, wherein said pesticidal composition further comprises a fungicide, bactericide, nematicide and/or insecticide.

6. The method according to claim 4, wherein said pesticidal composition further comprises a carrier, diluent, surfactant or adjuvant.

* * * * *